(12) United States Patent
Yamada et al.

(10) Patent No.: US 9,772,567 B1
(45) Date of Patent: Sep. 26, 2017

(54) COMPOUND, ELECTROPHOTOGRAPHIC PHOTORECEPTOR, AND PROCESS CARTRIDGE

(71) Applicant: FUJI XEROX CO., LTD., Tokyo (JP)

(72) Inventors: Wataru Yamada, Kanagawa (JP); Hidekazu Hirose, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/210,526

(22) Filed: Jul. 14, 2016

(30) Foreign Application Priority Data

Mar. 28, 2016 (JP) .................. 2016-064458

(51) Int. Cl.
*G03G 5/00* (2006.01)
*G03G 5/06* (2006.01)
(Continued)

(52) U.S. Cl.
CPC ......... *G03G 5/0609* (2013.01); *C07C 49/683* (2013.01); *G03G 5/0564* (2013.01);
(Continued)

(58) Field of Classification Search
CPC .............................. G03G 5/0609; C07C 49/683
See application file for complete search history.

(56) References Cited

U.S. PATENT DOCUMENTS 5,910,610 A  6/1999 Kobayashi et al.
5,989,765 A  11/1999 Kobayashi et al.
(Continued)

FOREIGN PATENT DOCUMENTS

JP  H06-123981 A  5/1994
JP  H08-295655 A  11/1996
(Continued)

*Primary Examiner* — Mark A Chapman
(74) *Attorney, Agent, or Firm* — Oliff PLC

(57) ABSTRACT

A compound has a structure represented by the following formula (C1):

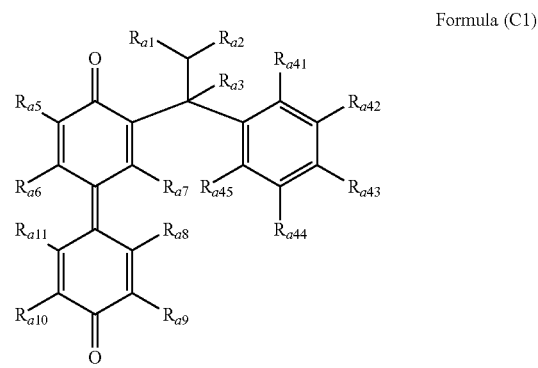

Formula (C1)

wherein $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ each independently represent a hydrogen atom, an alkyl group, an alkenyl group, an alkynyl group, an alkoxy group, an aralkyl group, an aryl group, a cyano group, a halogen atom, or a group obtained by combining two or more of the above groups, and a combination of $R_{a1}$ and $R_{a2}$, $R_{a41}$ and $R_{a42}$, $R_{a42}$ and $R_{a43}$, $R_{a43}$ and $R_{a44}$, $R_{a44}$ and $R_{a45}$, $R_{a5}$ and $R_{a6}$, $R_{a8}$ and $R_{a9}$, or $R_{a10}$ and $R_{a11}$ each independently may form a ring.

9 Claims, 6 Drawing Sheets

(51) Int. Cl.
*G03G 5/14* (2006.01)
*G03G 5/05* (2006.01)
*C07C 49/683* (2006.01)
*G03G 21/18* (2006.01)

(52) U.S. Cl.
CPC ......... *G03G 5/0614* (2013.01); *G03G 5/0696* (2013.01); *G03G 5/142* (2013.01); *G03G 21/18* (2013.01); *C07C 2101/14* (2013.01); *C07C 2101/16* (2013.01)

(56) References Cited

U.S. PATENT DOCUMENTS

| | | |
|---|---|---|
| 6,172,264 B1 | 1/2001 | Kobayashi et al. |
| 2005/0164106 A1 | 7/2005 | Bender et al. |

FOREIGN PATENT DOCUMENTS

| | | |
|---|---|---|
| JP | 2000-019747 A | 1/2000 |
| JP | 2005-215677 A | 8/2005 |
| JP | 2008-015208 A | 1/2008 |

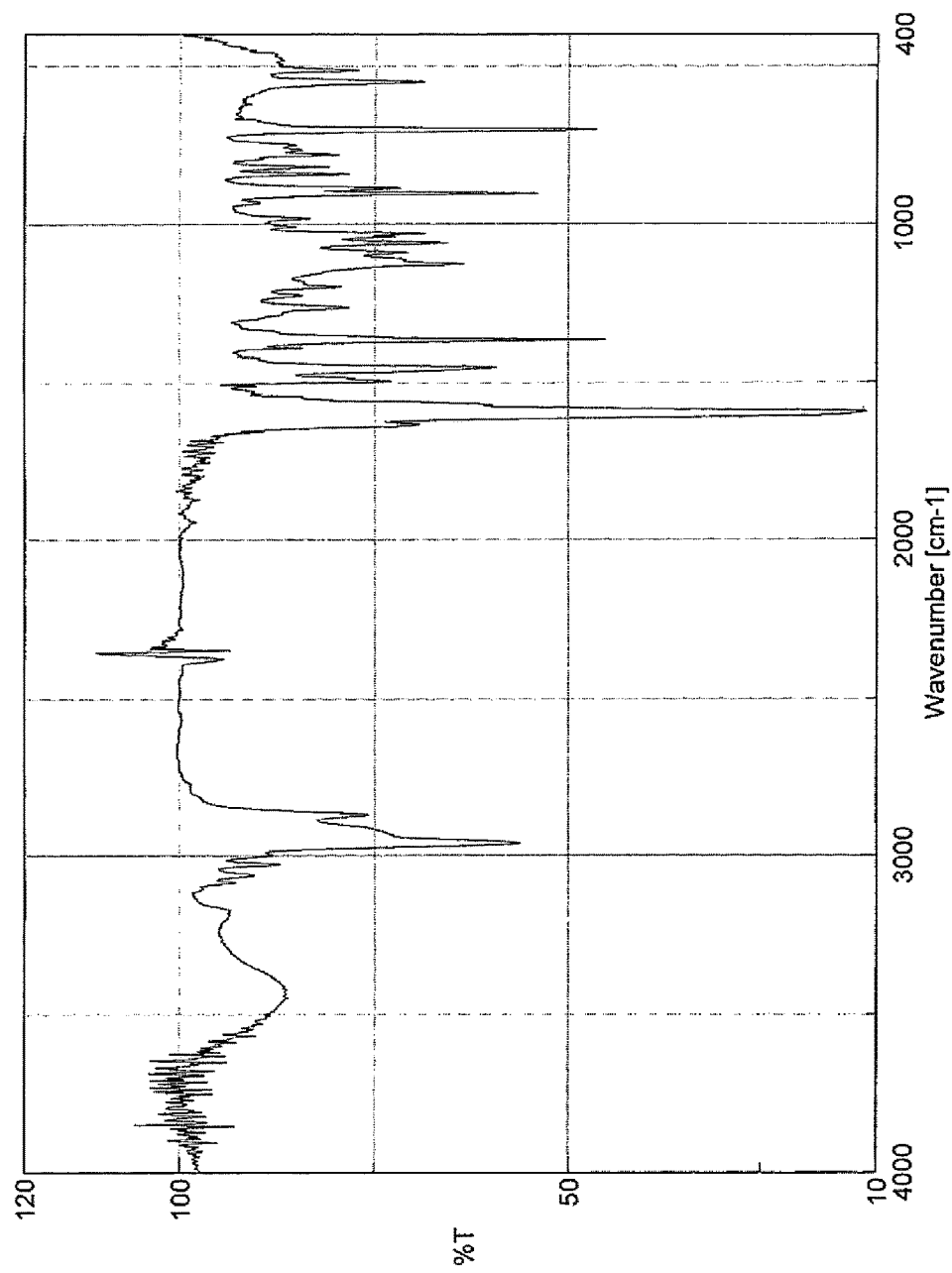

COMPOUND, ELECTROPHOTOGRAPHIC PHOTORECEPTOR, AND PROCESS CARTRIDGE

CROSS-REFERENCE TO RELATED APPLICATIONS

This application is based on and claims priority under 35 USC 119 from Japanese Patent Application No. 2016-064458 filed Mar. 28, 2016.

BACKGROUND

1. Technical Field

The present invention relates to a compound, an electrophotographic photoreceptor, and a process cartridge.

2. Related Art

In the related art, various materials are known as a charge transporting material which is used in an electrophotographic photoreceptor and the like.

SUMMARY

According to an aspect of the invention, there is provided a compound having a structure represented by the following formula (C1):

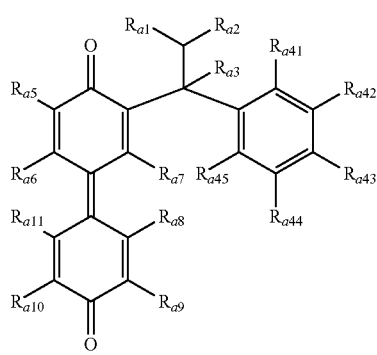

Formula (C1)

wherein $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ each independently represent a hydrogen atom, an alkyl group, an alkenyl group, an alkynyl group, an alkoxy group, an aralkyl group, an aryl group, a cyano group, a halogen atom, or a group obtained by combining two or more of the above groups, and a combination of $R_{a1}$ and $R_{a2}$, $R_{a41}$ and $R_{a42}$, $R_{a42}$ and $R_{a43}$, $R_{a43}$ and $R_{a44}$, $R_{a44}$ and $R_{a45}$, $R_{a5}$ and $R_{a6}$, $R_{a8}$ and $R_{a9}$, or $R_{a10}$ and $R_{a11}$ each independently may form a ring.

BRIEF DESCRIPTION OF THE DRAWINGS

Exemplary embodiments of the present invention will be described in detail based on the following figures, wherein:

FIG. 10 is a graph illustrating IR spectrum of Compound 17 synthesized in Example.

DETAILED DESCRIPTION

Figure 1:
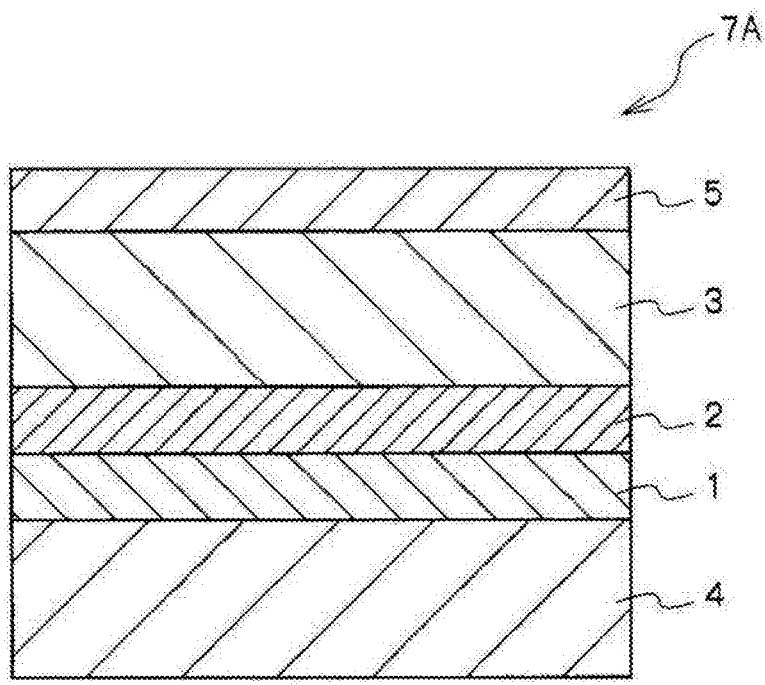
FIG. 1 is a schematic partial sectional view illustrating an example of a layer structure of an electrophotographic photoreceptor according to an exemplary embodiment.

Hereinafter, exemplary embodiments of the invention will be described in detail.

Compound

A compound according to an exemplary embodiment has a structure represented by the following formula (C1).

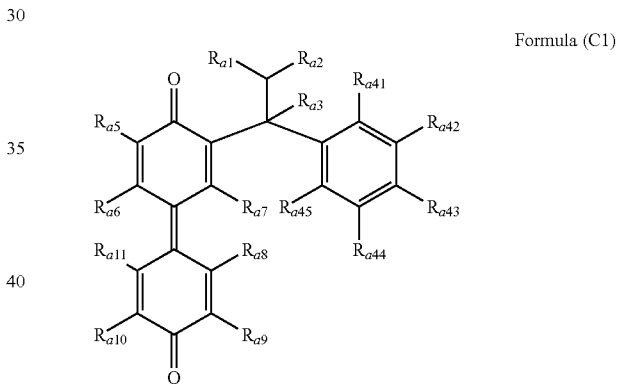

Formula (C1)

In the formula (C1), $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ each independently represent a hydrogen atom, an alkyl group, an alkenyl group, an alkynyl group, an alkoxy group, an aralkyl group, an aryl group, a cyano group, a halogen atom, and a group obtained by combining two or more of the above groups. $R_{a1}$ and $R_{a2}$, $R_{a41}$ and $R_{a42}$, $R_{a42}$ and $R_{a43}$, $R_{a43}$ and $R_{a44}$, $R_{a44}$ and $R_{a45}$, $R_{a5}$ and $R_{a6}$, $R_{a8}$ and $R_{a9}$, and $R_{a10}$ and $R_{a11}$ may independently form a ring.

According to the exemplary embodiment, there is provided a new compound having charge transporting capacity.

The compound which has the structure represented by the formula (C1) has excellent charge transporting capacity (at least one of electron transporting capacity and hole transporting capacity). The compound also has excellent compatibility with a resin.

Use

The compound according to the exemplary embodiment is appropriate for the purpose of requiring charge transporting properties, for example. For example, the compound according to the exemplary embodiment is used in forming a film in a photoelectric conversion device (organic EL device, electrophotographic photoreceptor, and the like), or in a solar cell, and an organic transistor.

Among the above uses, the compound is appropriate for a film (layer) which requires charge transporting properties and is present in an electrophotographic photoreceptor. Particularly, the compound is preferably used in an organic photosensitive layer, a single-layer type photosensitive layer (photosensitive layer having charge generating capacity and charge transporting capacity) of an electrophotographic photoreceptor, or an undercoat layer of a laminate type photoreceptor.

Here, the general single-layer type photosensitive layer is a layer in which a binder resin, a charge generating material, a hole transporting material, and an electron transporting material are contained as components. As the layer, there is a layer in which separation occurs by compatibility between the components.

The hole transporting material which is generally used has excellent compatibility with a binder resin which has low polarity. On the other hand, the electron transporting material has polarity lower than the hole transporting material, and causes separation. As a result, dispersibility of the electron transporting material may be lowered, and thus charging performance may be deteriorated.

On the contrary, the compound according to the exemplary embodiment is used as an electron transporting material in the single-layer type photosensitive layer, and thus an electrophotographic photoreceptor having excellent charging performance is obtained.

It is considered that this is because the compound having a structure which is represented by the formula (C1) has excellent compatibility with the binder resin having low polarity, and thus dispersibility in the single-layer type photosensitive layer is excellent. In addition, it is considered that this is because the compound represented by the formula (C1) has excellent electron transporting capacity.

Next, a structure of the compound according to the exemplary embodiment will be described in detail.

The compound according to the exemplary embodiment has a structure represented by the formula (C1). Among compounds having the structure represented by the formula (C1), a compound having a structure represented by the following formula (C2) is more preferable.

Structure represented by Formula (C1)

Each of the groups represented as $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a1}$, and $R_{a11}$ will be described.

An alkyl group may have any of a straight-chain shape, a branched shape, and a ring shape. The number of carbon atoms in a case where the alkyl group has a straight-chain shape or a branched shape is preferably from 1 to 20, and more preferably from 1 to 10. The number of carbon atoms in a case where the alkyl group has a ring shape is preferably from 3 to 10, and more preferably from 4 to 8. The alkyl group includes a substituted alkyl group and an unsubstituted alkyl group. Examples of the substituent are as follows.

Examples of the straight-chain alkyl group include a methyl group, an ethyl group, a propyl group, a butyl group, a pentyl group, a hexyl group, a heptyl group, and an octyl group.

Examples of the branched alkyl group include an i-propyl group, a t-butyl group, an isobutyl group, a sec-butyl group, an isopentyl group, a tert-pentyl group, a 2-pentyl group, a 3-pentyl group, and a 2-hexyl group.

Examples of the cyclic alkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

Examples of the substituted alkyl group include a halogeno substituted alkyl group of a group such as a monofluoromethyl group, a difluoromethyl group, a trifluoromethyl group, a mono-fluoroethyl group, a difluoroethyl group, a trifluoroethyl group, a chloromethyl group, a chloroethyl group, a dichloroethyl group, and isomers thereof; a group substituted with a hydroxyl group such as a hydroxymethyl group, a 1-hydroxyethyl group, a 2-hydroxyethyl group, a 1-hydroxypropyl group, a 2-hydroxypropyl group, a 3-hydroxypropyl group, and a 4-hydroxybutyl group; and a group substituted with an amino group such as an amino methyl group, and a 2-amino ethyl group.

As the preferable alkyl group, the methyl group, the ethyl group, the propyl group, the i-propyl group, the sec-butyl group, the t-butyl group, and the cyclohexyl group are exemplified.

The alkenyl group may have any of a straight-chain shape and a branched shape. The alkenyl group includes a substituted alkenyl group and an unsubstituted alkenyl group. Examples of the substituent are as follows.

Examples of the alkenyl group include a group such as a vinyl group, an allyl group, a propenyl group, a butenyl group, a pentenyl group, a hexenyl group, a heptenyl group, a butadienyl group, a hexatrienyl group, and isomers thereof.

The alkynyl group may have any of a straight-chain shape and a branched shape. The alkynyl group includes a substituted alkynyl group and an unsubstituted alkynyl group. Examples of the substituent are as follows.

As the alkynyl group, a straight-chain alkynyl group or a branched alkynyl group which has the number of carbon atoms of 2 to 6 is preferable. As an example, a group such as an ethynyl group, a propynyl group, a butynyl group, a pentynyl group, a hexynyl group, and isomers thereof.

An alkyl group in the alkoxy group may have any of a straight-chain shape, a branched shape, and a ring shape. The alkoxy group includes a substituted alkoxy group and an unsubstituted alkoxy group. Examples of the substituent are as follows. The preferable number of carbon atoms of the alkoxy group is the same as that in the descriptions for the alkyl group. An example of the preferable group is also the same as that in the descriptions for the alkyl group.

The aryl group may be any of a monocyclic group (group having only one aromatic ring), a polycyclic group (group in which two aromatic rings or more are bonded to each other), and a condensed cyclic group (group having a structure in which two aromatic rings or more share a side). The aryl group may be a heterocyclic group (group in which an element (heteroatom) other than carbon is provided in an aromatic ring). The number of carbon atoms (also including a heteroatom in an aromatic ring in a case of the heterocyclic type) is preferably from 5 to 20, and more preferably from 5 to 10. The aryl group includes a substituted aryl group and an unsubstituted aryl group. Examples of the substituent are as follows.

As an example of the monocyclic type aryl group, a group including a heteroatom, such as a phenyl group, a substituted phenyl group, a pyridine ring, a thiazole ring, a thiophene ring is exemplified.

Examples of the polycyclic type aryl group include a biphenyl group, and a terphenyl group.

Examples of the condensed cyclic type aryl group include a naphthyl group, an indenyl group, and an anthryl group.

Examples of the substituted aryl group include a tolyl group, a xylyl group, an indenyl group, a naphthyl group, a dimethyl naphthyl group, an anthryl group, a phenanthryl group, a fluorenyl group, a pyrenyl group, a chrysenyl group, and a naphthacenyl group.

As the preferable aryl group, the phenyl group, the biphenyl group, the naphthyl group, and the tolyl group.

An alkyl group in the aralkyl group may have any of a straight-chain shape, a branched shape, and a ring shape. The aralkyl group includes a substituted aryl group and an unsubstituted aryl group. Examples of the substituent are as follows. The preferable number of carbon atoms of the alkyl group is the same as that in the descriptions for the alkyl group. An example of the preferable group is also the same as that in the descriptions for the alkyl group.

An aryl group in the aralkyl group may have any of a monocyclic type, a polycyclic type, a condensed cyclic type, and a heterocyclic type. The aralkyl group may have a substituent and examples of the substituent are as follows. The preferable number of carbon atoms (including a heteroatom) of the aryl group is the same as that in the descriptions for the aryl group. An example of the preferable group is also the same as that in the descriptions for the aryl group.

As described above, among the compound having the structure represented by the formula (C1), a compound having a structure represented by the following formula (C2) is preferable. That is, the following group $R_{a101}$ is more preferable as a group represented by $R_{a10}$ in the formula (C1) among aralkyl groups.

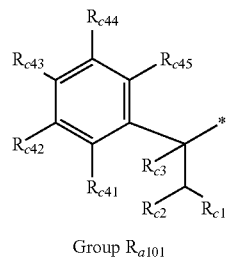

Group $R_{a101}$

Examples of the halogen atom include a fluorine atom, a chlorine atom, a bromine atom, and an iodine atom.

$R_{a1}$ and $R_{a2}$, $R_{a41}$ and $R_{a42}$, $R_{a42}$ and $R_{a43}$, $R_{a43}$ and $R_{a44}$, $R_{a44}$ and $R_{a45}$, $R_{a5}$ and $R_{a6}$, $R_{a8}$ and $R_{a9}$, and $R_{a10}$ and $R_{a11}$ may independently form a ring.

Examples of the ring include a cyclic alkyl group, and an aryl group. As the cyclic alkyl group, a group exemplified in the descriptions for the alkyl group is provided. As the aryl group, a group exemplified in the descriptions for the aryl group is provided.

As the ring, a phenyl group, a substituted phenyl group, and a cyclohexyl group are preferable.

Here, as the substituent which each group may be substituted with, an alkyl group, an alkoxy group, an aralkyl group, an aryl group, a cyano group, or a halogen atom is provided.

The groups represented by $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ may be groups obtained by bonding the above-described two groups or more to each other. That is, the groups may be groups obtained by bonding two groups or more which are selected from a group consisting of the alkyl group, the alkenyl group, the alkynyl group, the alkoxy group, the aralkyl group, the aryl group, the cyano group, and the halogen atom.

As $R_{a1}$ and $R_{a2}$, a hydrogen atom, a methyl group, a phenyl group, a naphthyl group, a methylphenyl group, a cyano group, a bromine atom, or a chlorine atom is preferable.

As $R_{a3}$, a hydrogen atom, a methyl group, or a phenyl group is preferable.

As $R_{a41}$ to $R_{a45}$, a hydrogen atom, a methyl group, a t-butyl group, or a ring (for example, phenyl group) which is formed by two of $R_{a41}$ to $R_{a45}$.

As $R_{a5}$, a group other than a hydrogen atom is preferable from a viewpoint of stability (prevention of decomposition) of a compound. For example, a straight-chain or branched alkyl group such as a methyl group, an i-propyl group, and a t-butyl group, a cyclic alkyl group such as a cyclohexyl group, or a ring (for example, aromatic ring such as a phenyl group) formed between $R_{a5}$ and $R_{a6}$ is preferable.

As $R_{a6}$, a hydrogen atom, an alkyl group, or a ring (for example, phenyl group) formed between $R_{a5}$ and $R_{a6}$ is preferable.

As $R_{a7}$, a hydrogen atom or an alkyl group is preferable.

As $R_{a8}$ and $R_{a11}$, a hydrogen atom, a straight-chain or branched alkyl group such as a methyl group, an i-propyl group, and a t-butyl group, a cyclic alkyl group such as a cyclohexyl group, or a ring (for example, phenyl group) formed between $R_{a9}$ and $R_{a10}$ is preferable.

As $R_{a9}$ and $R_{a10}$, a group other than a hydrogen atom is preferable from a viewpoint of stability (prevention of decomposition) and characteristics of a compound. For example, a straight-chain or branched alkyl group such as a methyl group, an i-propyl group, and a t-butyl group, a cyclic alkyl group such as a cyclohexyl group, or a ring (for example, aromatic ring such as a phenyl group) formed between $R_{a8}$ and $R_{a11}$ is preferable.

Structure represented by formula (C2)

Among compounds having a structure which is represented by the formula (C1), a compound having a structure which is represented by the following formula (C2) is preferable.

Formula (C2)

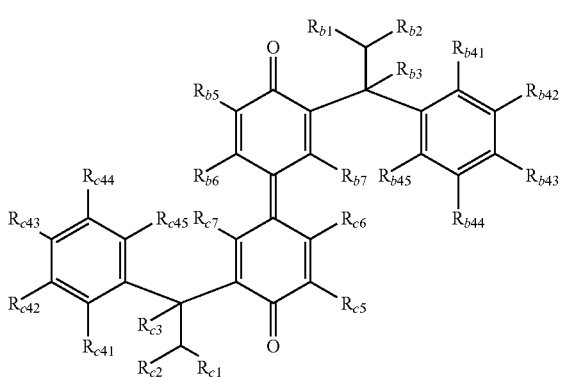

In the formula (C2), $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, $R_{b7}$, $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ each independently represent a hydrogen atom, an alkyl group, an alkenyl group, an alkynyl group, an alkoxy group, an aralkyl group, an aryl group, a cyano group, a halogen atom, and a group obtained by combining two or more of the above groups. $R_{b1}$ and $R_{b2}$, $R_{b41}$ and $R_{b42}$, $R_{b42}$ and $R_{b43}$, $R_{b43}$ and $R_{b44}$, $R_{b44}$ and $R_{b45}$, $R_{b5}$ and $R_{b6}$, $R_{c1}$ and $R_{c2}$, $R_{c41}$ and $R_{c42}$, $R_{c42}$ and $R_{c43}$, $R_{c43}$ and $R_{c44}$, $R_{c44}$ and $R_{c45}$, and $R_{c5}$ and $R_{c6}$ may independently form a ring.

In the formula (C2), a combination of $R_{b1}$ and $R_{c1}$, a combination of $R_{b2}$ and $R_{c2}$, a combination of $R_{b3}$ and $R_{c3}$, a combination of $R_{b41}$ and $R_{c41}$, a combination of $R_{b42}$ and $R_{c42}$, a combination of $R_{b43}$ and $R_{c43}$, a combination of $R_{b44}$ and $R_{c44}$, a combination of $R_{b45}$ and $R_{c45}$, a combination of $R_{b5}$ and $R_{c5}$, a combination of $R_{b6}$ and $R_{c6}$, and a combination of $R_{b7}$ and $R_{c7}$ may be the same as each other or be different from each other. All of the combinations are more preferably the same group.

The preferable forms of the groups (hydrogen atom, alkyl group, alkenyl group, alkynyl group, alkoxy group, aralkyl group, aryl group, cyano group, halogen atom, and group obtained by combining two or more of the above groups) represented by $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, $R_{b7}$, $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ in the formula (C2) are the same as those in the descriptions for the groups represented by $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ in the formula (C1).

The preferable group of $R_{b1}$ and $R_{c1}$ in the formula (C2) is the same as $R_{a1}$ in the formula (C1). The preferable groups of $R_{b2}$ and $R_{c2}$, $R_{b3}$ and $R_{c3}$, $R_{b41}$ and $R_{c41}$, $R_{b42}$ and $R_{c42}$, $R_{b43}$ and $R_{c43}$, $R_{b44}$ and $R_{c44}$, $R_{b45}$ and $R_{c45}$, $R_{b5}$ and $R_{c5}$, $R_{b6}$ and $R_{c6}$, and $R_{b7}$ and $R_{c7}$ in the formula (C2) each are the same as $R_{a2}$, $R_{a3}$, $R_{a41}$, $R_{a42}$, $R_{a43}$, $R_{a44}$, $R_{a45}$, $R_{a5}$, $R_{a6}$, and $R_{a7}$ in the formula (C1).

Here, a specific example of the compound having the structure which is represented by the formula (C1) will be described.

The meaning of marks in the following specific examples is as follows.

"Ph": phenyl group, "t-Bu": tertiary-butyl group, "c-Hex": cyclohexyl group, "1-Nft": 1-naphthyl group, and "4-MePh": 4-methyl phenyl group A part described so as to cross over two fields indicates that the two groups are bonded to each other, so as to form a ring.

Firstly, specific examples (Compounds 1 to 40) which have a structure represented by the formula (C2), and in which all of $R_{b1}$ and $R_{c1}$, $R_{b2}$ and $R_{c2}$, $R_{b3}$ and $R_{c3}$, $R_{b41}$ and $R_{c41}$, $R_{b42}$ and $R_{c42}$, $R_{b43}$ and $R_{c43}$, $R_{b44}$ and $R_{c44}$, $R_{b45}$ and $R_{c45}$, $R_{b5}$ and $R_{c5}$, $R_{b6}$ and $R_{c6}$, and $R_{b7}$ and $R_{c7}$ are the same group will be described below.

| Compound No | $R_{b1}$ $R_{c1}$ | $R_{b2}$ $R_{c2}$ | $R_{b3}$ $R_{c3}$ | $R_{b41}$ $R_{c41}$ | $R_{b42}$ $R_{c42}$ | $R_{b43}$ $R_{c43}$ | $R_{b44}$ $R_{c44}$ | $R_{b45}$ $R_{c45}$ | $R_{b5}$ $R_{c5}$ | $R_{b6}$ $R_{c6}$ | $R_{b7}$ $R_{c7}$ |
|---|---|---|---|---|---|---|---|---|---|---|---|
| 1 | H | H | H | H | H | $CH_3$ | H | H | t-Bu | H | H |
| 2 | H | H | H | $CH_3$ | H | $CH_3$ | H | $CH_3$ | t-Bu | H | H |
| 3 | H | H | H | H | H | H | H | H | $CH(CH_3)_2$ | H | H |
| 4 | H | H | H | H | H | H | H | H | Ph | H | H |
| 5 | H | H | H | H | H | H | H | H | $CH_3$ | H | H |
| 6 | $CH_3$ | $CH_3$ | H | H | H | H | H | H | $CH_3$ | H | H |
| 7 | H | H | $CH_3$ | H | H | H | H | H | c-Hex | H | H |
| 8 | H | H | $CH_3$ | H | H | H | H | H | $CH(CH_3)_2$ | H | H |
| 9 | H | H | $CH_3$ | H | H | H | H | H | Ph | H | H |
| 10 | H | H | $CH_3$ | H | H | H | H | H | $CH_3$ | H | H |
| 11 | H | H | $CH_3$ | H | H | H | H | H | t-Bu | H | H |
| 12 | H | H | H | H | $CH_3$ | H | H | H | $CH(CH_3)_2$ | H | H |
| 13 | H | H | H | $CH_3$ | H | H | H | H | c-Hex | H | H |
| 14 | Br | H | H | H | H | H | H | H | $CH(CH_3)_2$ | H | H |
| 15 | H | H | H | Ph | H | H | H | H | $CH(CH_3)_2$ | H | H |
| 16 | H | H | H | H | H | t-Bu | H | H | c-Hex | H | H |
| 17 | H | H | H | H | H | H | H | H | t-Bu | H | H |
| 18 | Ph | H | H | H | H | H | H | H | t-Bu | H | H |
| 19 | H | H | H | H | H | Cl | H | H | $CH(CH_3)_2$ | H | H |
| 20 | H | H | $CH_3$ | H | H | $CH_3$ | H | H | c-Hex | H | H |
| 21 | H | H | $CH_3$ | H | H | $CH_2Cl$ | H | H | t-Bu | H | H |
| 22 | H | H | H | H | H | H | H | H | c-Hex | H | H |
| 23 | H | H | $CH_3$ | H | Ph | H | H | H | c-Hex | H | H |
| 24 | 1-Nft | H | H | H | H | H | H | H | $CH_3$ | H | H |
| 25 | 4-MePh | H | H | H | H | $CH_3$ | H | H | t-Bu | H | H |
| 26 | CN | H | H | H | H | H | H | H | $CH(CH_3)_2$ | H | H |
| 27 | H | H | Ph | H | H | H | H | H | c-Hex | H | H |
| 28 | H | $CH_3$ | H | H | H | H | H | H | t-Bu | H | H |
| 29 | H | H | H | H | H | $CH_3$ | H | H | $CH(CH_3)_2$ | H | H |
| 30 | H | H | H | $CH_3$ | H | H | H | H | $CH(CH_3)_2$ | H | H |
| 31 | H | H | H | H | $CH_3$ | H | H | H | c-Hex | H | H |
| 32 | H | H | H | $CH_3$ | H | $CH_3$ | H | $CH_3$ | $CH(CH_3)_2$ | H | H |
| 33 | H | H | H | H | Ph | H | H | H | t-Bu | H | H |
| 34 | H | $CH_3$ | H | H | H | H | H | H | Ph | H | H |
| 35 | H | H | H | H | H | t-Bu | H | H | Ph | H | H |
| 36 | $CH_3$ | $CH_3$ | H | H | H | H | H | H | $CH(CH_3)_2$ | H | H |
| 37 | Ph | H | H | H | H | H | H | H | $CH(CH_3)_2$ | H | H |
| 38 | H | H | H | H | H | Cl | H | H | c-Hex | H | H |
| 39 | H | H | $CH_3$ | H | H | $CH_3$ | H | H | t-Bu | H | H |
| 40 | H | H | $CH_3$ | H | H | $CH_2Cl$ | H | H | Ph | H | H |

Next, specific examples (Compounds 101 to 110) which have a structure represented by the formula (C2), and in which at least some of $R_{b1}$ and $R_{c1}$, $R_{b2}$ and $R_{c2}$, $R_{b3}$ and $R_{c3}$, $R_{b41}$ and $R_{c41}$, $R_{b42}$ and $R_{c42}$, $R_{b43}$ and $R_{c43}$, $R_{b44}$ and $R_{c44}$, $R_{b45}$ and $R_{c45}$, $R_{b5}$ and $R_{c5}$, $R_{b6}$ and $R_{c6}$, and $R_{b7}$ and $R_{c7}$ are different will be described below.

| Compound No | $R_{b1}$ / $R_{c1}$ | $R_{b2}$ / $R_{c2}$ | $R_{b3}$ / $R_{c3}$ | $R_{b41}$ / $R_{c41}$ | $R_{b42}$ / $R_{c42}$ | $R_{b43}$ / $R_{c43}$ | $R_{b44}$ / $R_{c44}$ | $R_{b45}$ / $R_{c45}$ | $R_{b5}$ / $R_{c5}$ | $R_{b6}$ / $R_{c6}$ | $R_{b7}$ / $R_{c7}$ |
|---|---|---|---|---|---|---|---|---|---|---|---|
| 101 | H | H | H | H | H | H | H | H | c-Hex | H | H |
|  | H | H | H | H | H | H | H | H | t-Bu | H | H |
| 102 | H | H | H | H | H | $CH_3$ | H | H | t-Bu | H | H |
|  | H | H | H | H | H | H | H | H | t-Bu | H | H |
| 103 | H | H | H | H | H | $CH_3$ | H | H | t-Bu | H | H |
|  | H | H | $CH_3$ | H | H | H | H | H | t-Bu | H | H |
| 104 | H | H | $CH_3$ | H | H | H | H | H | t-Bu | H | H |
|  | H | H | $CH_3$ | H | H | H | H | H | t-Bu | H | H |
| 105 | H | H | H | $CH_3$ | H | H | H | H | $CH_3$ | H | H |
|  | H | H | H | H | H | H | H | H | t-Bu | H | H |
| 106 | H | H | H | H | $CH_3$ | H | H | H | $CH_3$ | H | H |
|  | H | H | H | H | H | H | H | H | $CH(CH_3)_2$ | H | H |
| 107 | H | H | H | $CH_3$ | H | $CH_3$ | H | $CH_3$ | $CH_3$ | H | H |
|  | H | H | H | H | H | H | H | H | t-Bu | H | H |
| 108 | H | H | H | Ph | H | H | H | H | $CH(CH_3)_2$ | H | H |
|  | H | H | H | H | H | H | H | H | t-Bu | H | H |
| 109 | H | $CH_3$ | H | H | H | H | H | H | t-Bu | H | H |
|  | H | H | H | H | H | H | H | H | t-Bu | H | H |
| 110 | $CH_3$ | $CH_3$ | H | H | H | H | H | H | $CH_3$ | H | H |
|  | H | H | H | H | H | H | H | H | t-Bu | H | H |

Specific examples (Compounds 201 to 210) which do not correspond to the formula (C2), and have a structure represented by the formula (C1) will be described below.

| Compound No | $R_{a1}$ | $R_{a2}$ | $R_{a3}$ | $R_{a41}$ | $R_{a42}$ | $R_{a43}$ | $R_{a44}$ | $R_{a45}$ | $R_{a5}$ | $R_{a6}$ | $R_{a7}$ | $R_{a8}$ | $R_{a9}$ | $R_{a10}$ | $R_{a11}$ |
|---|---|---|---|---|---|---|---|---|---|---|---|---|---|---|---|
| 201 | H | H | H | H | H | H | H | H | $CH(CH_3)_2$ | H | H | H | c-Hex | t-Bu | H |
| 202 | H | H | H | H | H | H | H | H | t-Bu | H | H | H | t-Bu | t-Bu | H |
| 203 | H | H | H | H | H | $CH_3$ | H | H | t-Bu | H | H | H | $CH_3$ | $CH_3$ | H |
| 204 | H | H | H | $CH_3$ | H | $CH_3$ | H | $CH_3$ | t-Bu | H | H | H | $CH(CH_3)_2$ | $CH(CH_3)_2$ | H |
| 205 | H | H | H | H | H | H | H | H | Ph |  | H |  | Ph | t-Bu | H |
| 206 | H | H | $CH_3$ | H | H | H | H | H | Ph |  | H |  | Ph | t-Bu | H |
| 207 | H | H | H | H | H | H | H | H | Ph |  | H |  | t-Bu | t-Bu | H |
| 208 | H | H | $CH_3$ | H | H | H | H | H | $CH(CH_3)_2$ | H | H | H | t-Bu | t-Bu | H |
| 209 | H | H | $CH_3$ | H | H | H | H | H | t-Bu | H | H | H | t-Bu | t-Bu | H |
| 210 | H | H | H | H | H | H | H | H | c-Hex | H | H | H | c-Hex | t-Bu | H |

Synthesis Method

Here, synthesis methods of the compound having the structure which is represented by the formula (C1) will be described in a form of a scheme.

(1) Scheme 1

Firstly, a synthesis method of a compound which have a structure represented by the formula (C2), and in which all of $R_{b1}$ and $R_{c1}$, $R_{b2}$ and $R_{c2}$, $R_{b3}$ and $R_{c3}$, $R_{b41}$ and $R_{c41}$, $R_{b42}$ and $R_{c42}$, $R_{b43}$ and $R_{c43}$, $R_{b44}$ and $R_{c44}$, $R_{b45}$ and $R_{c45}$, $R_{b5}$ and $R_{c5}$, $R_{b6}$ and $R_{c6}$, and $R_{b7}$ and $R_{c7}$ are the same group will be described.

In the scheme illustrated as follows, for convenience, all of $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, $R_{b7}$, $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ are described as "$R_A$".

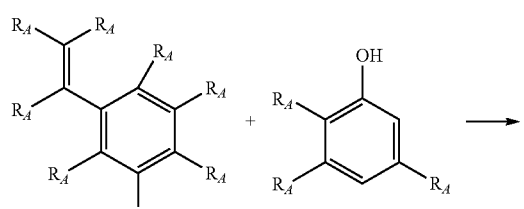

Raw material a1

Raw material a2

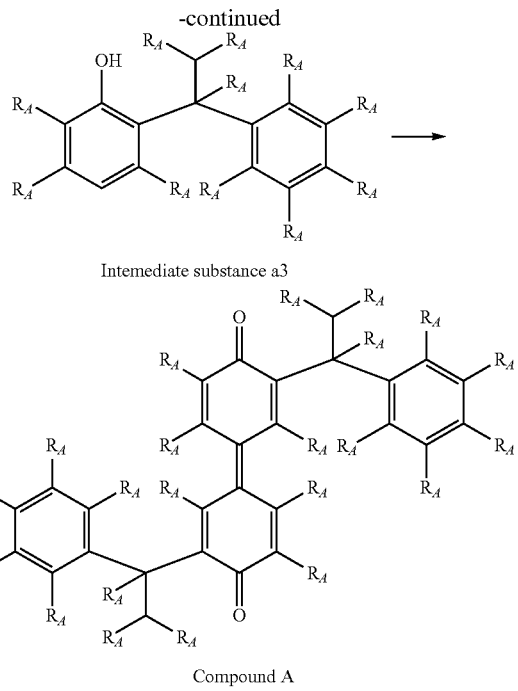

Intemediate substance a3

Compound A

A compound (for example, styrene) corresponding to a raw material a1, and a compound (for example, 1-naphthol) corresponding to a raw material a2 react with each other under the presence of a catalyst (for example, Al(O-i-Pr)$_3$), so that an intermediate substance a3 is obtained.

Then, intermediate substances a3 are caused to react with each other while oxygen is given (for example, while oxygen is caused to bubble in a liquid), and thus a compound A is synthesized.

Here, as the compound corresponding to the raw material a1, for example, raw materials a1-1 to a1-21 as follows are exemplified. As the compound corresponding to the raw material a2, for example, raw materials a2-1 to a2-5 as follows are exemplified.

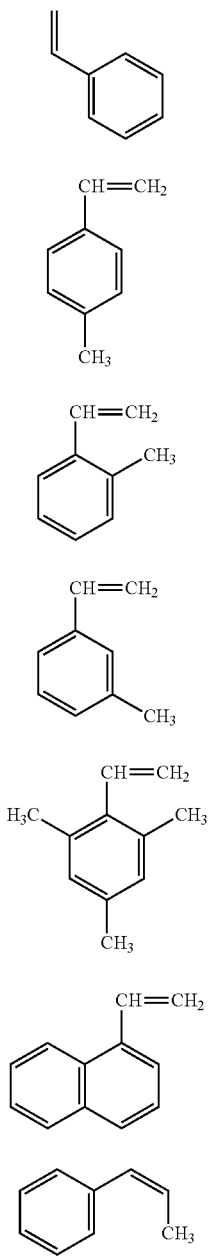

-continued

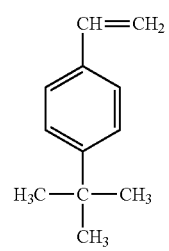 a1-8

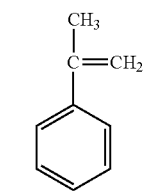 a1-9

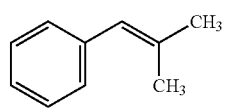 a1-10

 a1-11

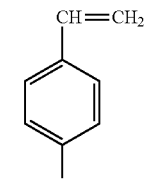 a1-12

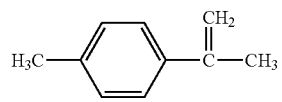 a1-13

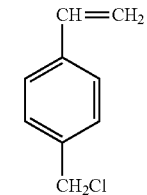 a1-14

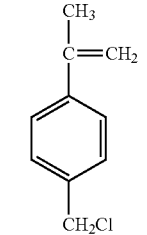 a1-15

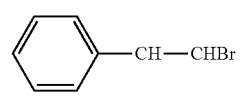 a1-16

-continued a1-17 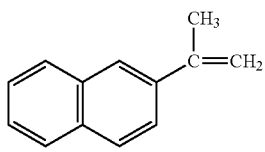

a1-18 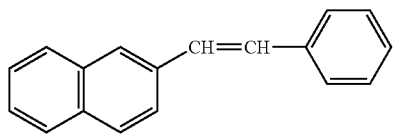

a1-19 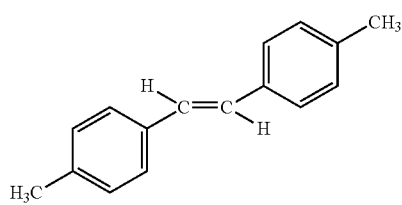

a1-20 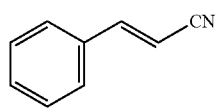

a1-21 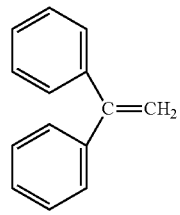

a2-1 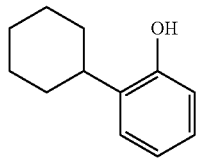

a2-2 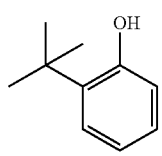

a2-3 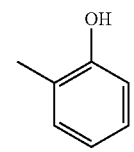

a2-4 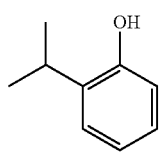

-continued a2-5 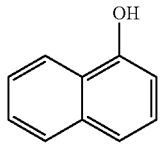

Next, a synthesis method of a compound which have a structure represented by the formula (C2), and in which at least some of $R_{b1}$ and $R_{c1}$, $R_{b2}$ and $R_{c2}$, $R_{b3}$ and $R_{c3}$, $R_{b41}$ and $R_{c41}$, $R_{b42}$ and $R_{c42}$, $R_{b43}$ and $R_{c43}$, $R_{b44}$ and $R_{c44}$, $R_{b45}$ and $R_{c45}$, $R_{b5}$ and $R_{c5}$, $R_{b6}$ and $R_{c6}$, and $R_{b7}$ and $R_{c7}$ are different will be described below.

In the scheme illustrated as follows, for convenience, all of $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, and $R_{b7}$ are described as "$R_A$", and all of $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ are described as "$R_B$".

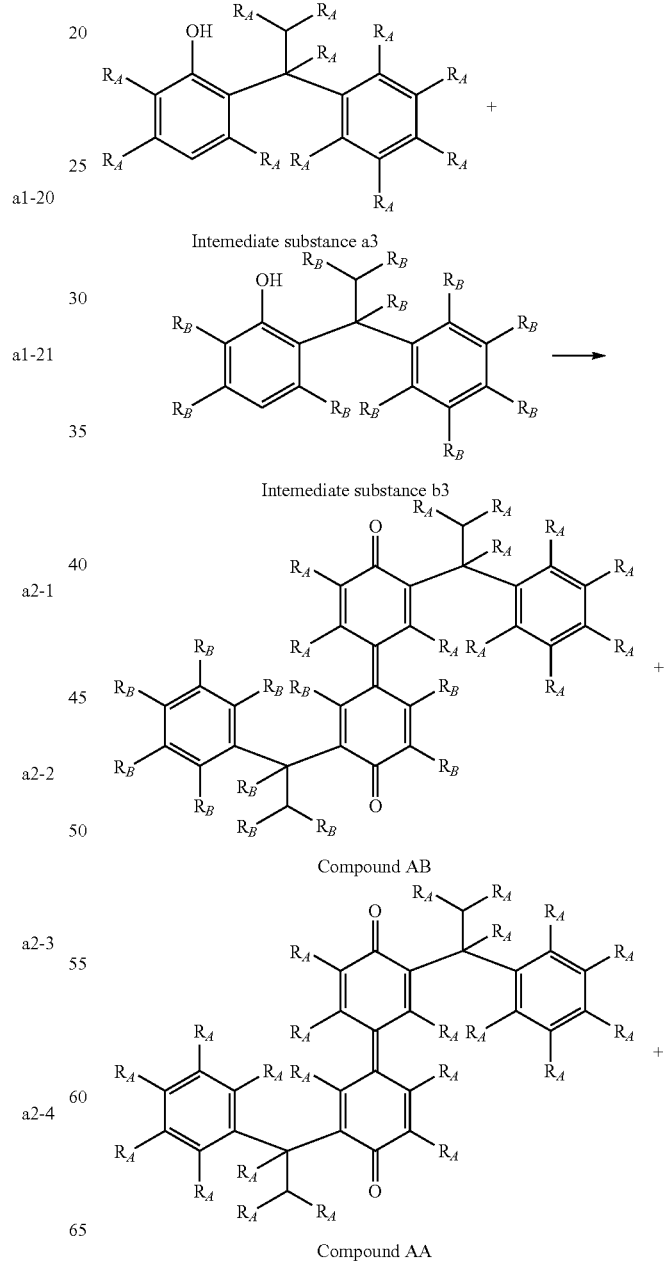

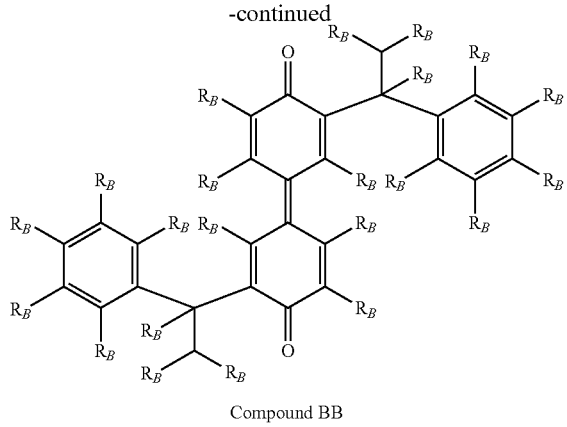

Compound BB

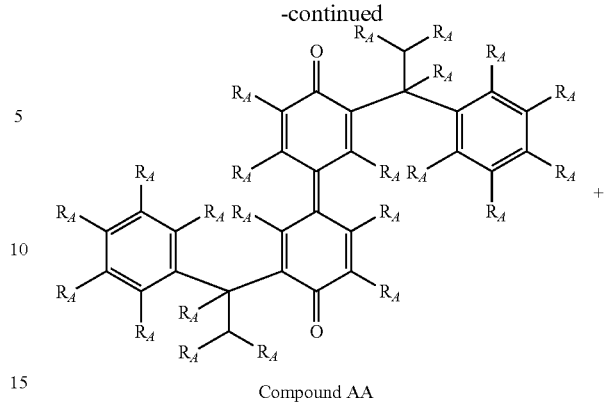

Compound AA

Similarly to the method described in Scheme 1, an intermediate substance a3 and an intermediate substance b3 are separately obtained. Then, a mixture of the intermediate substance a3 and the intermediate substance b3 is caused to react with oxygen while the oxygen is given (for example, while oxygen is caused to bubble in a liquid), and thus a mixture of a compound AB, a compound AA, and a compound BB is synthesized.

Then, refining may be performed. In this manner, the compound AB is obtained.

(3) Scheme 3

Next, a synthesis method of a compound which do not correspond to the formula (C2), and have a structure represented by the formula (C1) will be described.

In the scheme illustrated as follows, for convenience, all of $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, and $R_{a7}$ are described as "$R_A$", and all of $R_{a8}$, $R_{a9}$, $R_{a10}$ and $R_{a11}$ are described as "$R_C$".

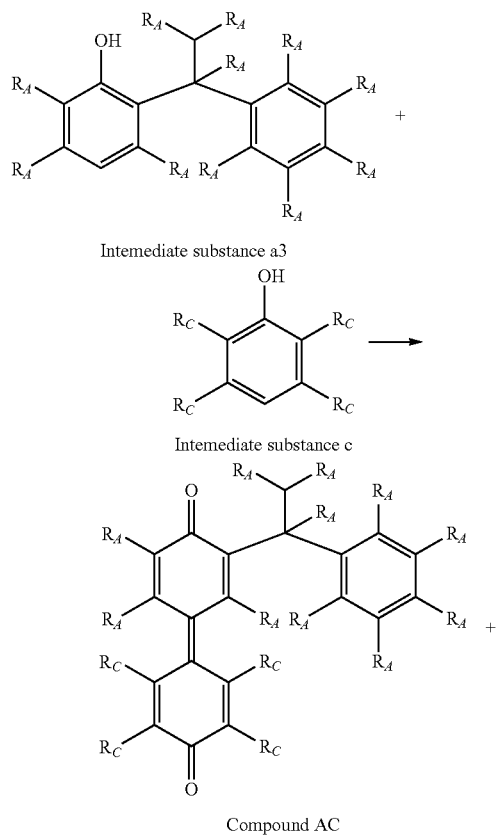

Compound AC

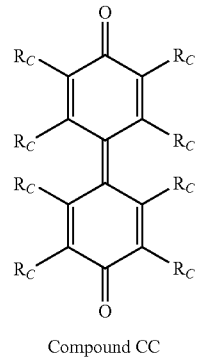

Compound CC

Similarly to the method described in Scheme 1, an intermediate substance a3 is obtained. Then, a mixture obtained by adding an intermediate substance c to the intermediate substance a3 is prepared. The mixture is caused to react while the oxygen is given (for example, while oxygen is caused to bubble in a liquid), and thus a mixture of a compound AC, a compound AA, and a compound CC is synthesized.

Then, refining may be performed. In this manner, the compound AC is obtained.

The compound according to the exemplary embodiment is used, for example, in forming a film in a photoelectric conversion device (organic EL device, electrophotographic photoreceptor, and the like) or in forming a solar cell, and an organic transistor.

Photoelectric Conversion Device

Next, a photoelectric conversion device using the compound according to the exemplary embodiment will be described.

Firstly, an electrophotographic photoreceptor which is an example of the photoelectric conversion device will be described.

Electrophotographic Photoreceptor

The electrophotographic photoreceptor according to the exemplary embodiment has a photosensitive layer which contains the compound having the structure which is represented by the formula (C1). The photosensitive layer is provided on an electroconductive substrate.

The electrophotographic photoreceptor according to the exemplary embodiment will be described in detail with reference to the drawings. In the drawings, the same or corresponding parts are denoted by the same reference signs, and duplicate descriptions thereof will be omitted.

Figure 2:
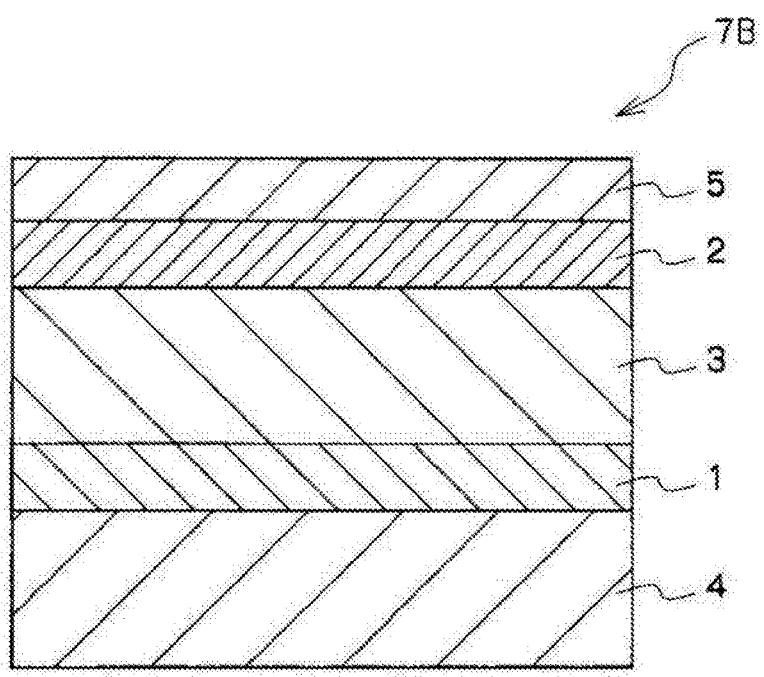
FIG. 2 is a schematic partial sectional view illustrating another example of the layer structure of the electrophotographic photoreceptor according to the exemplary embodiment.
Figure 3:
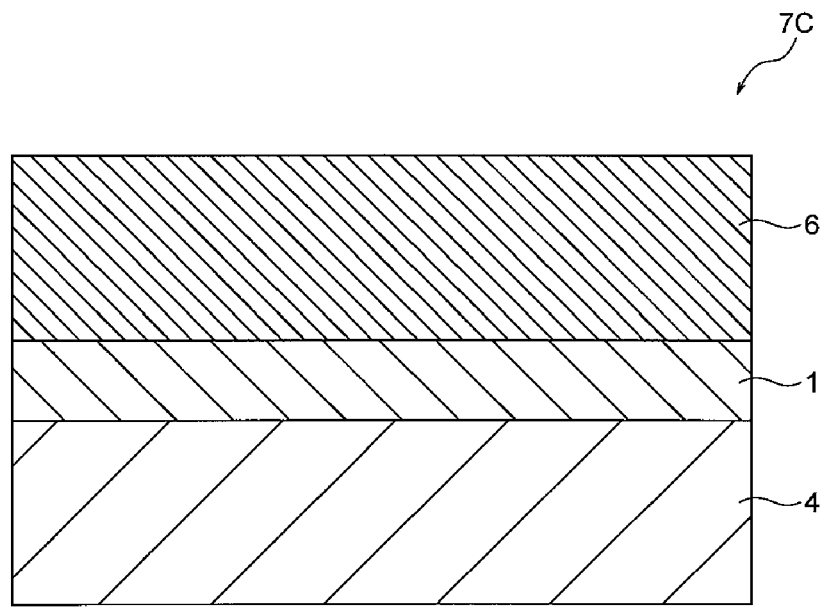
FIG. 3 is a schematic partial sectional view illustrating still another example of the layer structure of the electrophotographic photoreceptor according to the exemplary embodiment.

FIG. 1 is a schematic sectional view illustrating an appropriate example of a photoreceptor for electrophotography. FIGS. 2 and 3 are schematic sectional views illustrating examples of the electrophotographic photoreceptor according to other exemplary embodiments.

An electrophotographic photoreceptor 7A illustrated in FIG. 1 is a so-called function separation type photoreceptor (or laminate type photoreceptor). The electrophotographic photoreceptor 7A has a structure in which an undercoat layer 1 is provided on an electroconductive substrate 4, and a charge generating layer 2, a charge transport layer 3, and a protective layer 5 are sequentially formed on the undercoat layer 1. In the electrophotographic photoreceptor 7A, the charge generating layer 2 and the charge transport layer 3 constitute a photosensitive layer. For example, the undercoat layer 1 contains the compound having a structure which is represented by the formula (C1).

Similarly to the electrophotographic photoreceptor 7A illustrated in FIG. 1, an electrophotographic photoreceptor 7B illustrated in FIG. 2 is a function separation type photoreceptor in which a function is divided so as to be performed in the charge generating layer 2 and the charge transport layer 3.

The electrophotographic photoreceptor 7B illustrated in FIG. 2 has a structure in which the undercoat layer 1 is provided on the electroconductive substrate 4, and the charge transport layer 3, the charge generating layer 2, and the protective layer 5 are sequentially formed on the undercoat layer 1. In the electrophotographic photoreceptor 7B, the charge transport layer 3 and the charge generating layer 2 constitute a photosensitive layer. For example, the undercoat layer 1 contains the compound having a structure which is represented by the formula (C1).

An electrophotographic photoreceptor 7C illustrated in FIG. 3 contains a charge generating material and a charge transporting material in the same layer (single-layer type photosensitive layer 6). The electrophotographic photoreceptor 7C illustrated in FIG. 3 has a structure in which the undercoat layer 1 is provided on the electroconductive substrate 4, and the single-layer type photosensitive layer 6 is formed on the undercoat layer 1. In the electrophotographic photoreceptor 7C, for example, the single-layer type photosensitive layer 6 contains the compound having a structure which is represented by the formula (C1).

In the electrophotographic photoreceptors illustrated in FIGS. 1 to 3, the undercoat layer 1, the protective layer 5, and the like may be or may not be provided.

Regarding each of the layers of the electrophotographic photoreceptor according to the exemplary embodiment, an electrophotographic photoreceptor including the single-layer type photosensitive layer which is illustrated in FIG. 3 as a representative example will be described as an example. Descriptions will be made with reference signs omitted.

Electroconductive Substrate

Examples of the electroconductive substrate include metal plates, metal drums, and metal belts using metals (such as aluminum, copper, zinc, chromium, nickel, molybdenum, vanadium, indium, gold, and platinum), and alloys thereof (such as stainless steel). Further, other examples of the electroconductive substrate include papers, resin films, and belts which are coated, deposited, or laminated with a conductive compound (such as a conductive polymer and indium oxide), a metal (such as aluminum, palladium, and gold), or alloys thereof. The term "conductive" means that the volume resistivity is smaller than $10^{13}$ Ωcm.

When the electrophotographic photoreceptor is used in a laser printer, the surface of the electroconductive substrate is preferably roughened so as to have a centerline average roughness (Ra) of 0.04 μm to 0.5 μm sequentially to prevent interference fringes which are formed when irradiated by laser light. Further, when an incoherent light is used as a light source, surface roughening for preventing interference fringes is not particularly necessary, but occurrence of defects due to the irregularities on the surface of the electroconductive substrate is prevented, which is thus suitable for achieving a longer service life.

As the method for surface roughening, wet honing in which an abrasive is suspended in water and sprayed onto the support member, centerless grinding in which the electroconductive substrate is pressed on a rotating whetstone and grinding is continuously performed, an anodic oxidation treatment, and the like are included.

Other examples of the method for surface roughening include a method for surface roughening by forming a layer of a resin in which conductive or semiconductive particles are dispersed on the surface of an electroconductive substrate so that the surface roughening is achieved by the particles dispersed in the layer, without roughing the surface of the electroconductive substrate.

In the surface roughening treatment by anodic oxidation, an oxide film is formed on the surface of an electroconductive substrate by anodic oxidation in which a metal (for example, aluminum) electroconductive substrate as an anode is anodized in an electrolyte solution. Examples of the electrolyte solution include a sulfuric acid solution and an oxalic acid solution. However, the porous anodic oxide film formed by anodic oxidation without modification is chemically active, easily contaminated and has a large resistance variation depending on the environment. Therefore, it is preferable to conduct a sealing treatment in which fine pores of the anodic oxide film are sealed by cubical expansion caused by a hydration in pressurized water vapor or boiled water (to which a metallic salt such as a nickel salt may be added) to transform the anodic oxide into a more stable hydrated oxide.

The film thickness of the anodic oxide film is preferably from 0.3 μm to 15 μm. When the thickness of the anodic oxide film is within the above range, a barrier property against injection tends to be exerted and an increase in the residual potential due to the repeated use tends to be prevented.

The electroconductive substrate may be subjected to a treatment with an acidic aqueous solution or a boehmite treatment.

The treatment with an acidic treatment solution is carried out as follows. First, an acidic treatment solution including phosphoric acid, chromic acid, and hydrofluoric acid is prepared. The mixing ratio of phosphoric acid, chromic acid, and hydrofluoric acid in the acidic treatment solution is, for example, from 10% by weight to 11% by weight of phosphoric acid, from 3% by weight to 5% by weight of chromic acid, and from 0.5% by weight to 2% by weight of hydrofluoric acid. The concentration of the total acid components is preferably in the range of 13.5% by weight to 18% by weight. The treatment temperature is, for example, preferably from 42° C. to 48° C. The film thickness of the film is preferably from 0.3 μm to 15 μm.

The boehmite treatment is carried out by immersing the substrate in pure water at a temperature of 90° C. to 100° C. for 5 minutes to 60 minutes, or by bringing it into contact with heated water vapor at a temperature of 90° C. to 120° C. for 5 minutes to 60 minutes. The film thickness is preferably from 0.1 μm to 5 μm. The film may further be subjected to an anodic oxidation treatment using an electrolyte solution which sparingly dissolves the film, such as adipic acid, boric acid, borate, phosphate, phthalate, maleate, benzoate, tartrate, and citrate solutions.

Undercoat Layer

The undercoat layer is, for example, a layer including inorganic particles and a binder resin.

Examples of the inorganic particles include inorganic particles having powder resistance (volume resistivity) of about $10^2$ Ωcm to $10^{11}$ Ωcm.

Among these substances, as the inorganic particles having the resistance values above, metal oxide particles such as tin oxide particles, titanium oxide particles, zinc oxide particles, and zirconium oxide particles are preferable, and zinc oxide particles are more preferable.

The specific surface area of the inorganic particles as measured by a BET method is, for example, preferably is equal to or greater than 10 m$^2$/g.

The volume average particle diameter of the inorganic particles is, for example, preferably from 50 nm to 2,000 nm (preferably from 60 nm to 1,000 nm).

The content of the inorganic particles is, for example, preferably from 10% by weight to 80% by weight, and more preferably from 40% by weight to 80% by weight, based on the binder resin.

The inorganic particles may be the ones which have been subjected to a surface treatment. The inorganic particles which have been subjected to different surface treatments or have different particle diameters may be used in combination of two or more types.

Examples of the surface treatment agent include a silane coupling agent, a titanate coupling agent, an aluminum coupling agent, and a surfactant. Particularly, the silane coupling agent is preferable, and a silane coupling agent having an amino group is more preferable.

Examples of the silane coupling agent having an amino group include 3-aminopropyltriethoxysilane, N-2-(aminoethyl)-3-aminopropyltrimethoxysilane, N-2-(aminoethyl)-3-aminopropylmethyldimethoxysilane, and N,N-bis(2-hydroxyethyl)-3-aminopropyltriethoxysilane, but are not limited thereto.

A mixture of two or more types of the silane coupling agents may be used. For example, a silane coupling agent having an amino group and another silane coupling agent may be used in combination. Other examples of the silane coupling agent include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropyl methyl dimethoxy silane, N,N-bis(2-hydroxyethyl)-3-aminopropyl triethoxysilane, and 3-chloro-propyl trimethoxysilane. Examples of the silane coupling agent are not limited thereto.

The surface treatment method using a surface treatment agent may be any one of known methods, and may be either of a dry method and a wet method.

The amount of the surface treatment agent for treatment is, for example, preferably from 0.5% by weight to 10% by weight, based on the inorganic particles.

Here, inorganic particles and an electron acceptive compound (acceptor compound) are preferably included in the undercoat layer from the viewpoint of superior long-term stability of electrical characteristics and carrier blocking property.

Examples of the electron acceptive compound include electron transporting materials such as quinone compounds such as chloranil and bromanil; tetracyanoquinodimethane compounds; fluorenone compounds such as 2,4,7-trinitrofluorenone and 2,4,5,7-tetranitro-9-fluorenone; oxadiazole compounds such as 2-(4-biphenyl)-5-(4-t-butylphenyl)-1,3,4-oxadiazole, 2,5-bis(4-naphthyl)-1,3,4-oxadiazole, and 2,5-bis(4-diethylaminophenyl)-1,3,4-oxadiazole; xanthone compounds; thiophene compounds; and diphenoquinone compounds such as 3,3',5,5'-tetra-t-butyldiphenoquinone.

Particularly, as the electron acceptive compound, compounds having an anthraquinone structure are preferable. As the electron acceptive compounds having an anthraquinone structure, hydroxyanthraquinone compounds, aminoanthraquinone compounds, aminohydroxyanthraquinone compounds, and the like are preferable, and specifically, anthraquinone, alizarin, quinizarin, anthrarufin, purpurin, and the like are preferable.

The electron acceptive compound may be included as dispersed with the inorganic particles in the undercoat layer, or may be included as attached to the surface of the inorganic particles.

Examples of the method of attaching the electron acceptive compound to the surface of the inorganic particles include a dry method and a wet method.

The dry method is a method for attaching an electron acceptive compound to the surface of the inorganic particles, in which the electron acceptive compound is added dropwise to the inorganic particles or sprayed thereto together with dry air or nitrogen gas, either directly or in the form of a solution in which the electron acceptive compound is dissolved in an organic solvent, while the inorganic particles are stirred with a mixer or the like having a high shearing force. The addition or spraying of the electron acceptive compound is preferably carried out at a temperature no higher than the boiling point of the solvent. After the addition or spraying of the electron acceptive compound, the inorganic particles may further be subjected to baking at a temperature of 100° C. or higher. The baking may be carried out at any temperature and timing without limitation, by which desired electrophotographic characteristics may be obtained.

The wet method is a method for attaching an electron acceptive compound to the surface of the inorganic particles, in which the inorganic particles are dispersed in a solvent by means of stirring, ultrasonic wave, a sand mill, an attritor, a ball mill, or the like, then the electron acceptive compound is added and the mixture is further stirred or dispersed, and thereafter, the solvent is removed. As a method for removing the solvent, the solvent is removed, for example, by filtration or distillation. After removing the solvent, the particles may further be subjected to baking at a temperature of 100° C. or higher. The baking may be carried out at any temperature and timing without limitation, in which desired electrophotographic characteristics may be obtained. In the wet method, the moisture contained in the inorganic particles may be removed prior to adding the electron acceptive compound, and examples of a method for removing the moisture include a method for removing the moisture by stirring and heating the inorganic particles in a solvent or by azeotropic removal with the solvent.

Furthermore, the attachment of the electron acceptive compound may be carried out before or after the inorganic particles are subjected to a surface treatment using a surface treatment agent, and the attachment of the electron acceptive compound may be carried out at the same time with the surface treatment using a surface treatment agent.

The content of the electron acceptive compound may be, for example, from 0.01% by weight to 20% by weight. The content thereof is preferably from 0.01% by weight to 10% by weight, based on the inorganic particles.

Examples of the binder resin used in the undercoat layer include known materials, such as well-known polymeric compounds such as acetal resins (for example, polyvinylbutyral and the like), polyvinyl alcohol resins, polyvinyl acetal resins, casein resins, polyamide resins, cellulose resins, gelatins, polyurethane resins, polyester resins, unsaturated polyether resins, methacrylic resins, acrylic resins, polyvinyl chloride resins, polyvinyl acetate resins, vinyl chloride-vinyl acetate-maleic anhydride resins, silicone resins, silicone-alkyd resins, urea resins, phenol resins, phenol-formaldehyde resins, melamine resins, urethane resins, alkyd resins, and epoxy resins; zirconium chelate compounds; titanium chelate compounds; aluminum chelate compounds; titaniumalkoxide compounds; organic titanium compounds; and silane coupling agents.

Other examples of the binder resin used in the undercoat layer include charge transporting resins having charge transporting groups, and conductive resins (for example, polyaniline and the like).

Among these substances, as the binder resin used in the undercoat layer, a resin which is insoluble in a coating solvent of an upper layer is suitable, and particularly, resins obtained by reacting thermosetting resins such as urea resins, phenol resins, phenol-formaldehyde resins, melamine resins, urethane resins, unsaturated polyester resins, alkyd resins, and epoxy resins; and resins obtained by a reaction of at least one kind of resin selected from the group consisting of polyamide resins, polyester resins, polyether resins, methacrylic resins, acrylic resins, polyvinyl alcohol resins, and polyvinyl acetal resins with curing agents are suitable.

In the case where these binder resins are used in combination of two or more types thereof, the mixing ratio is set as appropriate.

The undercoat layer may contain the electron transporting material. It is preferable that the compound according to the exemplary embodiment, that is, the compound having a structure which is represented by the above-described formula (C1) is used as the electron transporting material.

Other electron transporting materials may be used together. For example, an electron transporting material as follows is exemplified: quinone compounds such as p-benzoquinone, chloranil, bromanil, anthraquinone; tetracyanoquinodimethane compounds; fluorenone compounds such as 2,4,7-trinitrofluorenone; xanthone compounds; benzophenone compounds; cyanovinyl compounds; and ethylene compounds.

Specifically, electron transporting materials of ET-1 to ET-9 which will be described in section (of a single-layer type photosensitive layer) (which will be described later) are exemplified.

The content of the electron transporting material may be, for example, from 1% by weight to 70% by weight, with respect to the all solid components. The content thereof is preferably from 5% by weight to 40% by weight, and more preferably from 10% by weight to 30% by weight.

Various additives may be used for the undercoat layer to improve electrical characteristics, environmental stability, or image quality.

Examples of the additives include known materials such as the polycyclic condensed type or azo type of the electron transporting pigments, zirconium chelate compounds, titanium chelate compounds, aluminum chelate compounds, titanium alkoxide compounds, organic titanium compounds, and silane coupling agents. A silane coupling agent, which is used for surface treatment of inorganic particles as described above, may also be added to the undercoat layer as an additive.

Examples of the silane coupling agent as an additive include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropyl methyl methoxy silane, N,N-bis(2-hydroxyethyl)-3-aminopropyl triethoxysilane, and 3-chloropropyl trimethoxysilane.

Examples of the zirconium chelate compounds include zirconium butoxide, zirconium ethylacetoacetate, zirconium triethanolamine, acetylacetonate zirconium butoxide, ethylacetoacetate zirconium butoxide, zirconium acetate, zirconium oxalate, zirconium lactate, zirconium phosphonate, zirconium octanoate, zirconium naphthenate, zirconium laurate, zirconium stearate, zirconium isostearate, methacrylate zirconium butoxide, stearate zirconium butoxide, and isostearate zirconium butoxide.

Examples of the titanium chelate compounds include tetraisopropyl titanate, tetranormalbutyl titanate, butyl titanate dimer, tetra(2-ethylhexyl) titanate, titanium acetyl acetonate, polytitaniumacetyl acetonate, titanium octylene glycolate, titanium lactate ammonium salt, titanium lactate, titanium lactate ethyl ester, titanium triethanol aminate, and polyhydroxy titanium stearate.

Examples of the aluminum chelate compounds include aluminum isopropylate, monobutoxy aluminum diisopropylate, aluminum butylate, diethylacetoacetate aluminum diisopropylate, and aluminum tris(ethylacetoacetate).

These additives may be used singly, or as a mixture or a polycondensate of two or more types thereof.

The Vickers hardness of the undercoat layer is preferably equal to or greater than 35.

The surface roughness of the undercoat layer (ten point height of irregularities) is adjusted in the range of $1/(4n)$ (n represents a refractive index of an upper layer) of a wavelength $\lambda$ to $(1/2)\lambda$. The wavelength $\lambda$ represents a wavelength of the laser for exposure and n represents a refractive index of the upper layer, in order to prevent a moire image.

Resin particles and the like may be added in the undercoat layer in order to adjust the surface roughness. Examples of the resin particles include silicone resin particles and cross-linked polymethyl methacrylate resin particles. In addition, the surface of the undercoat layer may be polished in order to adjust the surface roughness. Examples of the polishing method include buffing grinding, a sandblasting treatment, wet honing, and a grinding treatment.

The formation of the undercoat layer is not particularly limited, and well-known forming methods are used. However, the formation of the undercoat layer is carried out by, for example, forming a coating film of a coating liquid for forming an undercoat layer, the coating liquid obtained by adding the components above to a solvent, and drying the coating film, followed by heating, as desired.

Examples of the solvent for preparing the coating liquid for forming the undercoat layer include alcohol solvents, aromatic hydrocarbon solvents, hydrocarbon halide solvents, ketone solvents, ketone alcohol solvents, ether solvents, and ester solvents.

Examples of these solvents include general organic solvents such as methanol, ethanol, n-propanol, iso-propanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, and toluene.

Examples of a method for dispersing inorganic particles in preparing the coating liquid for forming an undercoat layer include known methods such as methods using a roll mill, a ball mill, a vibration ball mill, an attritor, a sand mill, a colloid mill, a paint shaker, and the like.

As a method of coating the electroconductive substrate with the coating liquid for forming an undercoat layer, general methods such as a blade coating method, a wire bar coating method, a spraying method, a dip coating method, a bead coating method, an air knife coating method, a curtain coating method, and the like are exemplified.

The film thickness of the undercoat layer is set to, for example, preferably be equal to or greater than 15 μm, and is set to be more preferably in a range of 20 μm to 50 μm.

Intermediate Layer

Although not shown in the drawings, an intermediate layer may be provided between the undercoat layer and the photosensitive layer.

The intermediate layer is, for example, a layer including a resin. Examples of the resin used in the intermediate layer include polymeric compounds such as acetal resins (for example polyvinylbutyral), polyvinyl alcohol resins, polyvinyl acetal resins, casein resins, polyamide resins, cellulose resins, gelatins, polyurethane resins, polyester resins, methacrylic resins, acrylic resins, polyvinyl chloride resins, polyvinyl acetate resins, vinyl chloride-vinyl acetate-maleic anhydride resins, silicone resins, silicone-alkyd resins, phenol-formaldehyde resins, and melamine resins.

The intermediate layer may be a layer including an organic metal compound. Examples of the organic metal compound used in the intermediate layer include organic metal compounds containing a metal atom such as zirconium, titanium, aluminum, manganese, and silicon.

These compounds used in the intermediate layer may be used singly or as a mixture or a polycondensate of plural compounds.

Among these substances, layers containing organometallic compounds containing a zirconium atom or a silicon atom are preferable.

The formation of the intermediate layer is not particularly limited, and well-known forming methods are used. However, the formation of the intermediate layer is carried out, for example, by forming a coating film of a coating liquid for forming an intermediate layer, the coating liquid obtained by adding the components above to a solvent, and drying the coating film, followed by heating, as desired.

As a coating method for forming an intermediate layer, general methods such as a dip coating method, an extrusion coating method, a wire bar coating method, a spraying method, a blade coating method, a knife coating method, and a curtain coating method are used.

The film thickness of the intermediate layer is set to, for example, preferably from 0.1 μm to 3 μm. Further, the intermediate layer may be used as an undercoat layer.

Single-layer type photosensitive layer

The single-layer type photosensitive layer contains a binder resin (a), a charge generating material (b), a hole transporting material (c), and an electron transporting material (d), for example. The single-layer type photosensitive layer may further contain an additive in addition to the above materials.

Binder Resin (a)

Examples of the binder resin used in the single-layer type photosensitive layer include polycarbonate resins, polyester resins, polyarylate resins, methacrylic resins, acrylic resins, polyvinyl chloride resins, polyvinylidene chloride resins, polystyrene resins, polyvinyl acetate resins, styrene-butadiene copolymers, vinylidene chloride-acrylonitrile copolymers, vinyl chloride-vinyl acetate copolymers, vinyl chloride-vinyl acetate-maleic anhydride copolymer, silicone resins, silicone alkyd resins, phenol-formaldehyde resins, styrene-alkyd resins, poly-N-vinylcarbazole, and polysilane. Among the substances, the polycarbonate resins or the polyarylate resins are appropriate as the binder resin. The binder resin is singly used or is used in combination of two or more types thereof.

Charge Generating Material (b)

Examples of the charge generating material include azo pigments such as bisazo and trisazo pigments; condensed aromatic pigments such as dibromoanthanthrone pigments; perylene pigments; pyrrolopyrrole pigments; phthalocyanine pigments; zinc oxides; and trigonal selenium.

Among the substances, in order to correspond to laser exposure in the near-infrared region, it is preferable to use metal phthalocyanine pigments or nonmetal phthalocyanine pigments as the charge generating material.

Among the substances, at least one selected from a group consisting of hydroxy gallium phthalocyanine pigments and chlorogallium phthalocyanine pigments is preferably used as the charge generating material.

Hydroxy Gallium Phthalocyanine Pigments

The hydroxy gallium phthalocyanine pigment is not particularly limited thereto. A V-type hydroxy gallium phthalocyanine pigment may be used.

Particularly, for example, a hydroxy gallium phthalocyanine pigment which has the maximum peak wavelength in a range from 810 nm to 839 nm in the spectral absorption spectrum of a range from 600 nm to 900 nm is preferably used as the hydroxy gallium phthalocyanine pigment, from a viewpoint of obtaining excellent dispersibility. In a case where the hydroxy gallium phthalocyanine pigment is used as a material of the electrophotographic photoreceptor, it is easy to obtain excellent dispersibility, sufficient sensitivity, charging characteristics, and dark attenuation characteristics.

In the hydroxy gallium phthalocyanine pigment which has the maximum peak wavelength in the range from 810 nm to 839 nm, it is preferable that an average particle diameter is in a specific range, and a BET specific surface area is in a specific range. Specifically, the average particle diameter is preferably equal to or less than 0.20 μm, and more preferably from 0.01 μm to 0.15 μm. The BET specific surface area is preferably equal to or more than 45 $m^2/g$, more preferably equal to or more than 50 $m^2/g$, and particularly preferably from 55 $m^2/g$ to 120 $m^2/g$.

The average particle diameter is a volume average particle diameter (d50 average particle diameter) and has a value measured by a laser diffraction/scattering particle diameter distribution measurement device (LA-700, product manufactured by Horiba Ltd.). The average particle diameter has a value measured by using a nitrogen substitution method with a BET type specific surface area measurement device (product manufactured by Shimadzu Corporation: FLOWSORB II2300).

Here, the average particle diameter is equal to or less than 0.20 μm, and a specific surface area value is equal to or less than 45 $m^2/g$, and thus coarsening of a pigment particle is prevented, and forming the aggregate of pigment particles is prevented. Characteristics of dispersibility, sensitivity, charging characteristics, and dark attenuation characteristics are improved. Accordingly, the occurrence of an image defect is prevented.

The maximum particle diameter (maximum value of primary particle diameters) of the hydroxy gallium phthalocyanine pigment is preferably equal to or less than 1.2 μm, more preferably equal to or less than 1.0 μm, and further preferably equal to or less than 0.3 μm. If the maximum particle diameter is equal to or less than the above range, an occurrence of black spots is prevented.

Regarding the hydroxy gallium phthalocyanine pigment, from a viewpoint of preventing an occurrence of density unevenness, it is preferable that the average particle diameter is equal to or less than 0.2 μm, the maximum particle diameter is equal to or less than 1.2 μm, and the specific surface area value is equal to or more than 45 m²/g. The density unevenness is caused by exposing a photoreceptor in a fluorescent lamp and the like.

It is preferable that the hydroxy gallium phthalocyanine pigment is a V type which has a diffraction peak at a position at which the Bragg angle (2θ±0.20) in the X-ray diffraction spectrum using a Cukα characteristic X-ray is at least 7.3°, 16.0°, 24.9°, and 28.0°.

Chlorogallium Phthalocyanine Pigment

The chlorogallium phthalocyanine pigment is not particularly limited thereto, but a substance in which excellent sensitivity as an electrophotographic photoreceptor material, and which has a diffraction peak at a position at which the Bragg anglde (2θ±0.20) is 7.4°, 16.6°, 25.5°, and 28.3° is preferably used.

The maximum peak wavelength of an appropriate spectral absorption spectrum of the chlorogallium phthalocyanine pigment, and the average particle diameter, the maximum particle diameter, and the specific surface area value of the chlorogallium phthalocyanine pigment are similar to those of the hydroxy gallium phthalocyanine pigment.

The total content percentage of the two types of charge generating materials is preferably from 0.8% by weight to 1.5% by weight, with respect to the photosensitive layer. The total content percentage is equal to or less than the upper limit value, and thus aggregation in the charge generating layer in the photosensitive layer is prevented. The total content percentage is equal to or more than the lower limit value, and thus charge generating capacity required in the photoreceptor is easily exhibited.

The upper limit value is preferably equal to or less than 1.4% by weight, more preferably equal to or less than 1.25% by weight, and further preferably equal to or less than 1.2% by weight. The lower limit value is preferably equal to or more than 1.05% by weight and more preferably equal to or more than 1.15% by weight.

In a case where the hydroxy gallium phthalocyanine pigment and the chlorogallium phthalocyanine pigment are used together in the photosensitive layer, the content ratio of the hydroxy gallium phthalocyanine pigment and the chlorogallium phthalocyanine pigment is preferably in a range of 2:8 to 8:2, more preferably in a range of 4:6 to 7:3, and further preferably in a range of 5:5 to 6:4.

The content ratio is in the above range, and thus aggregation in the charge generating layer in the photosensitive layer is prevented.

Hole Transporting Material (c)

As the hole transporting material, a hole transporting material such as triarylamine compounds, benzidine compounds, arylalkane compounds, aryl substituted ethylene compounds, stilbene compounds, anthracene compounds, and hydrazone compounds is exemplified.

The compound according to the exemplary embodiment, that is, the compound having the structure which is represented by the above-described formula (C1) may be used as the hole transporting material.

The hole transporting material is singly used or is used in combination of two or more types thereof, but it is not limited thereto.

From a viewpoint of charge mobility, a triaryl amine derivative represented by the following formula (B-1) and a benzidine derivative represented by the following formula (B-2) are preferable as the hole transporting material.

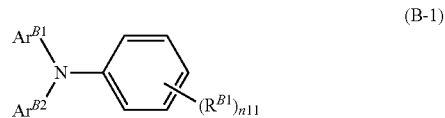

(B-1)

In the formula (B-1), $R^{B1}$ represents a hydrogen atom or a methyl group. n11 represents 1 or 2. $Ar^{B1}$ and $Ar^{B2}$ each independently represent a substituted or unsubstituted aryl group, —$C_6H_4$—$C(R^{B3})$=$C(R^{B4})(R^{B5})$, or —$C_6H_4$—CH=CH—CH=$C(R^{B6})(R^{B7})$. $R^{B3}$ to $R^{B7}$ each independently represent a hydrogen atom, a substituted or unsubstituted alkyl group, or a substituted or unsubstituted aryl group.

Examples of the substituent include a halogen atom, an alkyl group having 1 to 5 carbon atoms, an alkoxy group having 1 to 5 carbon atoms, and a substituted amino group which is substituted with an alkyl group having 1 to 3 carbon atoms.

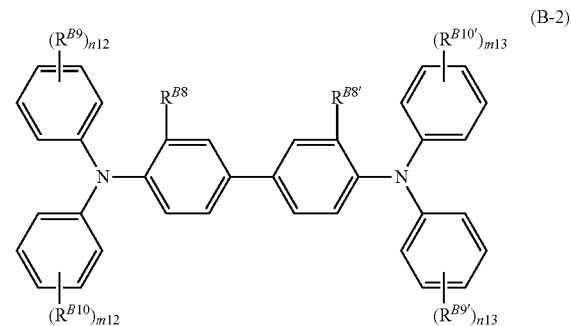

(B-2)

In the formula (B-2), $R^{B8}$ and $R^{B8'}$ may be the same as each other or be different from each other. $R^{B8}$ and $R^{B8'}$ each represent a hydrogen atom, a halogen atom, an alkyl group having 1 to 5 carbon atoms, and an alkoxy group having 1 to 5 carbon atoms. $R^{B9}$, $R^{B9'}$, $R^{B10}$, and $R^{B10'}$ may be the same as each other or be different from each other. $R^{B9}$, $R^{B9'}$, $R^{B10}$, and $R^{B10'}$ each represent a hydrogen atom, a halogen atom, an alkyl group having 1 to 5 carbon atoms, an alkoxy group having 1 to 5 carbon atoms, an amino group which is substituted with an alkyl group having 1 to 2 carbon atoms, a substituted or unsubstituted aryl group, —$C(R^{B11})$=$C(R^{B12})(R^{B13})$, and —CH=CH—CH=$C(R^{B14})(R^{B15})$. $R^{B11}$ to $R^{B13}$ each represent a hydrogen atom, a substituted or unsubstituted alkyl group, and a substituted or unsubstituted aryl group. m12, m13, n12, and n13 each represent an integer of 0 to 2.

Here, among the triarylamine derivatives represented by the formula (B-1) and the benzidine derivatives represented by the formula (B-2), triarylamine derivatives having "—C₆H₄—CH=CH—CH=C(R^{B6})(R^{B7})" and benzidine derivatives having "—CH=CH—CH=C(R^{B14})(R^{B15})" are particularly preferable.

As a specific example of the hole transporting material which contains the triarylamine derivatives represented by the formula (B-1) and the benzidine derivatives represented by the formula (B-2), and is used for the photosensitive layer in the exemplary embodiment, the following compound is exemplified.

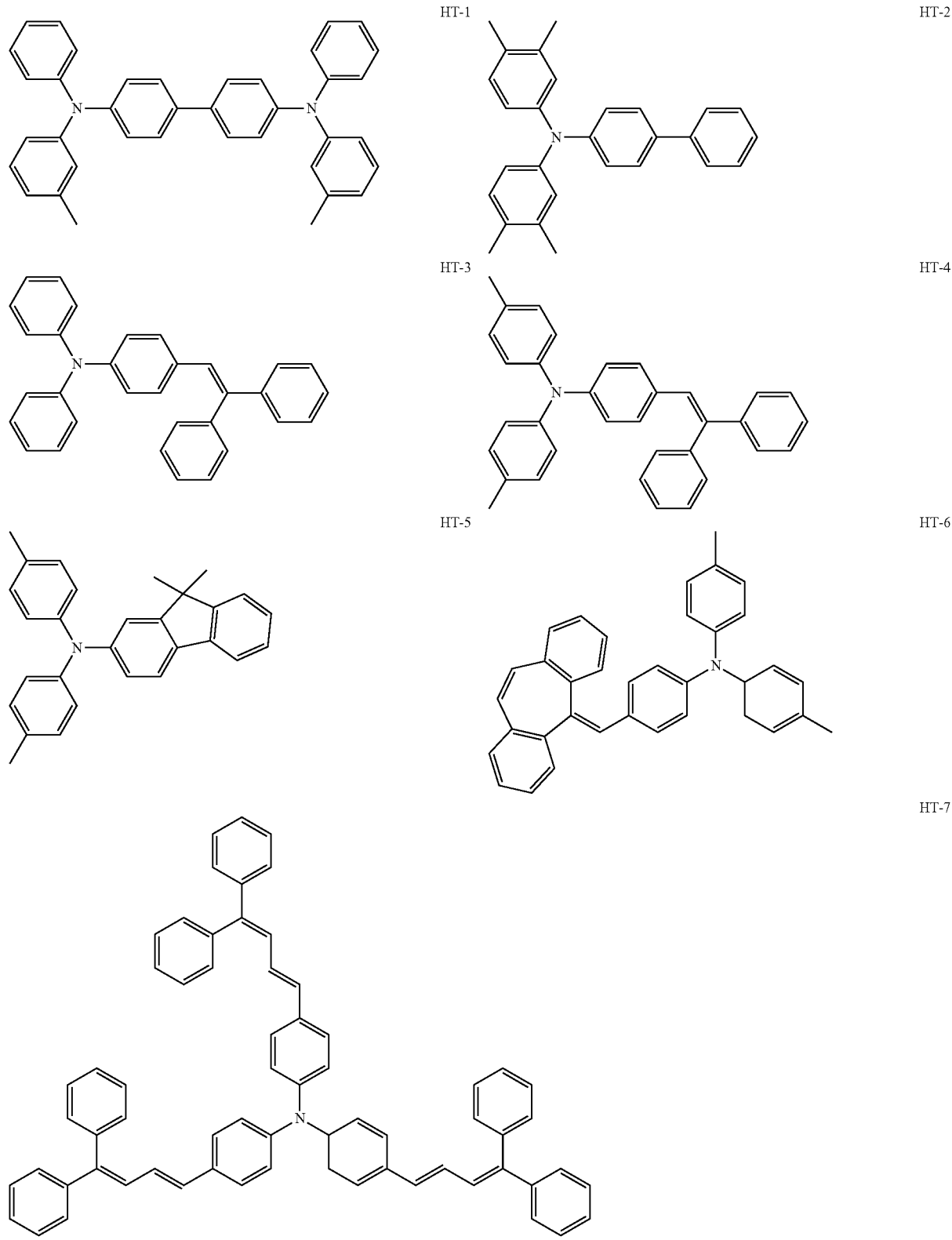

-continued

HT-8

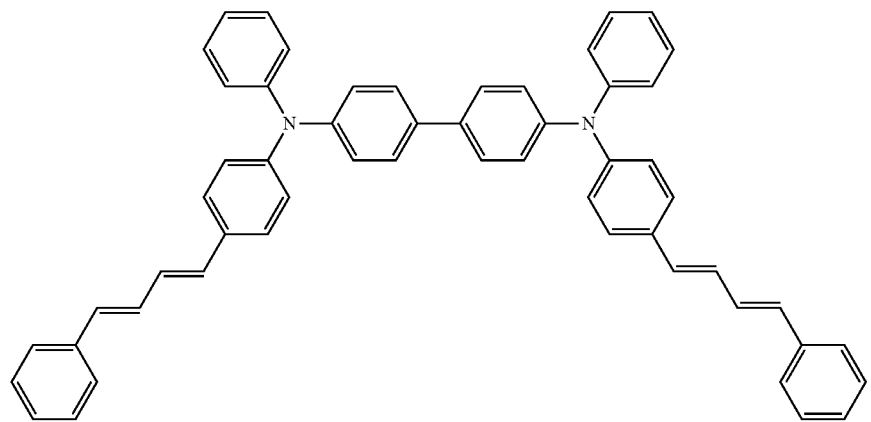

HT-9

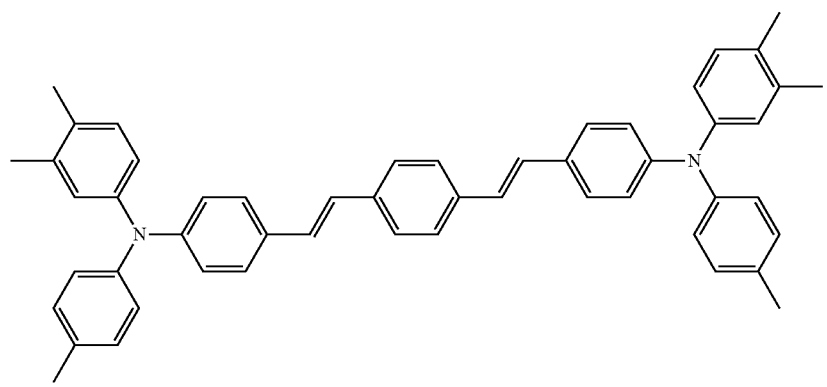

HT-10

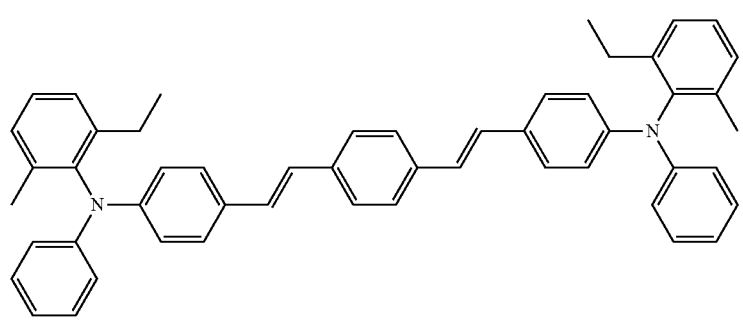

HT-11

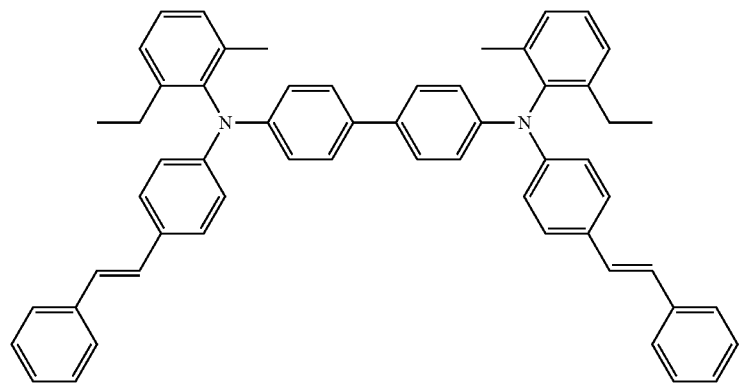

The content of the hole transporting material may be, for example, from 10% by weight to 50% by weight, with respect to the all solid components of the single-layer photosensitive layer. The content thereof is preferably from 20% by weight to 40% by weight.

The weight ratio of the hole transporting material and the compound represented by formula (C1) (the hole transporting material:the compound) contained in the photosensitive layer is in a range of 1:1 to 9:1.

Electron Transporting Material (d)

It is preferable that the compound according to the exemplary embodiment, that is, the compound having a structure which is represented by the above-described formula (C1) is used as the electron transporting material.

Other electron transporting materials may be used together. For example, an electron transporting material as follows is exemplified: quinone compounds such as p-benzoquinone, chloranil, bromanil, anthraquinone; tetracyanoquinodimethane compounds; fluorenone compounds such as 2,4,7-trinitrofluorenone; xanthone compounds; benzophenone compounds; cyanovinyl compounds; and ethylene compounds.

Specifically, the following electron transporting materials of ET-1 to ET-9 are exemplified.

ET-1
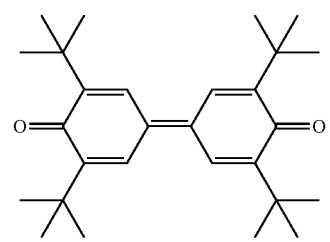

ET-2
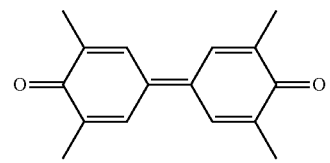

ET-3
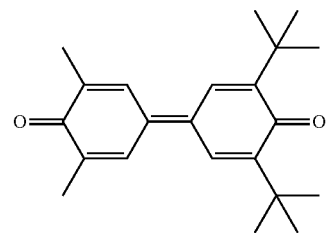

ET-4
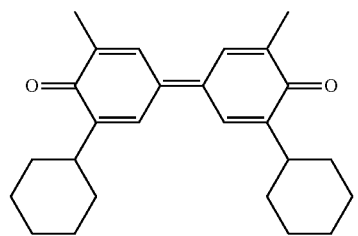

ET-5
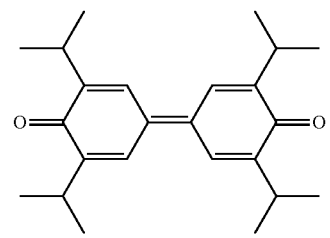

ET-6
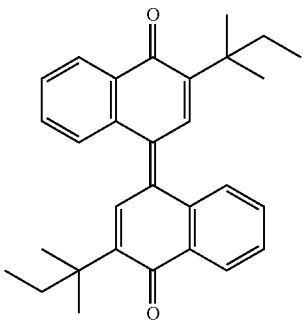

ET-7
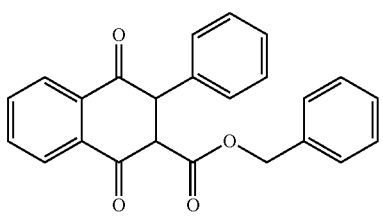

ET-8
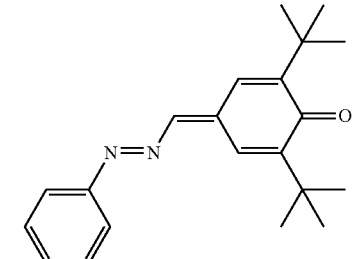

ET-9
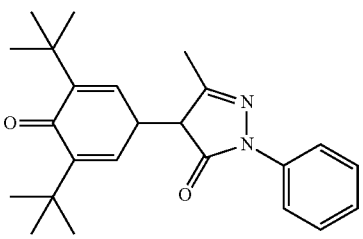

The content of the electron transporting material may be from 5% by weight to 40% by weight, with respect to all solid components of the single-layer type photoreceptor. The content thereof is preferably from 10% by weight to 30% by weight. The content of the electron transporting material is in the above range with respect to all of the solid components of the single-layer typephotoreceptor, and thus the electrical characteristics of the photoreceptor becomes better in comparison to a case where the content is less than the above range. In addition, deterioration of the electrical characteristics is prevented, and an occurrence of blushing and black spots in the formed image is prevented in comparison to a case where the content is more than the range.

The total amount of the compound having the structure which is represented by the formula (C1) is preferably equal to or more than 5% by weight, and more equal to or more than 30% by weight, with respect to the entirety of the electron transporting material.

Ratio of Hole Transporting Material and Electron Transporting Material

A ratio of the hole transporting material and the electron transporting material is preferably from 50:50 to 90:10, and more preferably from 60:40 to 80:20, in a weight ratio (hole transporting material:electron transporting material).

It is preferable that at least one of the triaryl amine derivative represented by the formula (B-1) and a benzidine derivative represented by the following formula (B-2) are used as the hole transporting material, and the compound (compound having the structure which is represented by the formula (C1)) according to the exemplary embodiment is used as the electron transporting material.

Other Additive

The single-layer type photosensitive layer may contain well-known other additives such as an oxidation inhibitor, a photostabilizer, and a thermal stabilizer. In a case where the single-layer type photosensitive layer functions as a surface layer, the single-layer type photosensitive layer may contain fluororesin particles, silicone oil, and the like.

Formation of Single-Layer Type Photosensitive Layer

The single-layer type photosensitive layer is formed by using a coating liquid for forming a photosensitive layer which is obtained by adding the component to a solvent.

As the solvent, a general organic solvent is exemplified. Examples of the general organic solvent include aromatic hydrocarbons such as benzene, toluene, xylene, and chlorobenzene; ketones such as acetone and 2-butanone; halogenated aliphatic hydrocarbons such as methylene chloride, chloroform, and ethylene chloride; cyclic or straight-chain ethers such as tetrahydrofuran and ethyl ether. The solvent is used singly or is used in combination of two or more types thereof.

A media dispersing machine or a medialess dispersing machine is used for a method of dispersing particles (for example, charge generating material) in the coating layer for forming a photosensitive layer. Examples of the media dispersing machine include a ball mill, a vibrating ball mill, an attritor, a sand mill, and a horizontal sand mill. Examples of the medialess dispersing machine include a stirrer, an ultrasonic dispersing machine, a roll mill, and a high-pressure homogenizer. Examples of the high-pressure homogenizer include a collision system in which the particles are dispersed by causing the dispersion liquid to collide against liquid or against walls under a high pressure, and a penetration system in which the particles are dispersed by causing the dispersion liquid to penetrate through a fine flow path under a high pressure.

Examples of a method of coating an undercoat layer with the coating liquid for forming a photosensitive layer include a dip coating method, an extrusion coating method, a wire bar coating method, a spraying method, a blade coating method, a knife coating method, and a curtain coating method.

The film thickness of the single-layer type photosensitive layer is preferably from 5 μm to 60 μm, and more preferably from 10 μm to 50 μm.

Protective Layer

A protective layer is provided on the photosensitive layer, if necessary. The protective layer is provided, for example, in order to prevent the chemical change of the photosensitive layer during charging or to further improve mechanical strength of the photosensitive layer.

Thus, a layer constituted by a cured film (cross-linked film) may be applied as the protective layer. As the layer, for example, a layer indicated by the following 1) or the following 2) is exemplified.

1) Layer constituted by a cured film of a composition which contains a reactive group-containing charge transporting material in which a reactive group and a charge transporting skeleton are provided in the same molecule (that is, layer which contains a polymer or a cross-linked substance of the reactive group-containing charge transporting material)

2) Layer constituted by a cured film of a composition which contains a non-reactive charge transporting material and a reactive group-containing non-charge transporting material in which a reactive group is provided without the charge transporting skeleton (that is, layer which contains the non-reactive charge transporting material and a polymer or a cross-linked substance of the reactive group-containing non-charge transporting material)

As the reactive group of the reactive group-containing charge transporting material, well-known reactive groups are exemplified. Examples of the well-known reactive groups include a chain polymerizing group, an epoxy group, —OH, —OR (where R represents an alkyl group], —NH$_2$, —SH, —COOH, —SiR$^{Q3}_{3-Qn}$(OR$^{Q2}$)$_{Qn}$ (where R$^{Q1}$ represents a hydrogen atom, an alkyl group, or a substituted or unsubstituted aryl group. R$^{Q2}$ represents a hydrogen atom, an alkyl group, and a trialkylsilyl group. Qn indicates an integer of 1 to 3.

The chain polymerizing group is not particularly limited as long as the chain polymerizing group is a functional group which may perform radical polymerization. For example, the chain polymerizing group is a functional group having a group which has at least a carbon double bond. Specifically, as the chain polymerizing group, for example, a group which contains at least one selected from a vinyl group, a vinyl ether group, a vinyl thioether group, a styryl group (vinyl phenyl group), an acryloyl group, a methacryloyl group, and derivatives thereof, are exemplified. Among the groups, as the chain polymerizing group, a group which contains at least one selected from vinyl group, a styryl group (vinyl phenyl group), an acryloyl group, a methacryloyl group, and derivatives thereof is preferably used because of excellent reactivity thereof.

The charge transporting skeleton of the reactive group-containing charge transporting material is not particularly limited as long as the skeleton is a well-known structure in the electrophotographic photoreceptor. For example, the charge transporting skeleton is a skeleton derived from a fluorine-containing hole transporting compound such as a triarylamine compound, a benzidine compound, and a hydrazone compound. As the charge transporting skeleton, a skeleton conjugated with a nitrogen atom is exemplified. Among the skeletons, a triarylamine skeleton is preferable.

The reactive group-containing charge transporting material which has a reactive group and a charge transporting skeleton, and a non-reactive charge transporting material, and a reactive group-containing non-charge transporting material may be selected from known materials.

In addition, the protective layer may contain a known additive.

Forming the protective layer is not particularly limited, and a known forming method is used. However, for example, a film is formed by using a coating liquid for forming a protective layer which is obtained by adding the above components to a solvent, and the coating film is dried, and curing processing, for example, heating is performed if necessary.

Examples of a solvent for preparing the coating liquid for forming a protective layer include an aromatic solvent such as toluene and xylene; ketone solvent such as methyl ethyl ketone, methyl isobutyl ketone, and cyclohexanone; an ester solvent such as ethyl acetate and butyl acetate; ether solvent such as tetrahydrofuran and dioxane; a cellosolve solvent such as ethylene glycol monomethyl ether; and an alcohols solvent such as isopropyl alcohol and butanol. The solvent is singly used or is used in combination of two or more types thereof.

The coating liquid for forming a protective layer may be a solventless coating liquid.

As a method of coating the photosensitive layer (for example, charge transport layer) with the coating liquid for forming a protective layer, a general method is exemplified. Examples of the general method include a dip coating method, an extrusion coating method, a wire bar coating method, a spraying method, a blade coating method, a knife coating method, and a curtain coating method.

The film thickness of the protective layer is preferably set to be in a range of 1 µm to 20 µm, and more preferably set to be in a range of 2 µm to 10 µm, for example.

Image Forming Apparatus (and Process Cartridge)

An image forming apparatus according to the exemplary embodiment includes an electrophotographic photoreceptor, a charging unit, an electrostatic latent image forming unit, a developing unit, and a transfer unit. The charging unit charges a surface of the electrophotographic photoreceptor. The electrostatic latent image forming unit forms an electrostatic latent image on the charged surface of the electrophotographic photoreceptor. The developing unit develops the electrostatic latent image formed on the surface of the electrophotographic photoreceptor by using a developer containing the toner, so as to form a toner image. The transfer unit transfers the toner image onto a surface of a recording medium. The electrophotographic photoreceptor according to the exemplary embodiment is applied as the above electrophotographic photoreceptor.

As the image forming apparatus according to this exemplary embodiment, a well-known image forming apparatus is applied: an apparatus including a fixing unit for fixing a toner image transferred onto a surface of a recording medium; a direct transfer type apparatus that directly transfers a toner image formed on a surface of an electrophotographic photoreceptor onto a recording medium; an intermediate transfer type apparatus that primarily transfers a toner image formed on a surface of an electrophotographic photoreceptor onto a surface of an intermediate transfer member, and then secondarily transfers the toner image which is primarily transferred onto the surface of the intermediate transfer member onto a surface of the recording medium; an apparatus including a cleaning unit that performs cleaning on a surface of an electrophotographic photoreceptor before charging after a toner image is transferred; an apparatus including a neutralization unit that performs neutralization by irradiating a surface of an electrophotographic photoreceptor before charging with neutralizing light after a toner image is transferred; an apparatus including an electrophotographic photoreceptor heating member for increasing the temperature of the electrophotographic photoreceptor and reducing the relative temperature.

In the case of the intermediate transfer type device, for example, a configuration which has an intermediate transfer member, a primary transfer unit, and a secondary transfer unit is applied for the transfer unit. The intermediate transfer member has a surface to the surface of which the toner image is transferred. The primary transfer unit primarily transfers a toner image formed on the surface of the electrophotographic photoreceptor to the surface of the intermediate transfer member. The secondary transfer unit secondarily transfers the toner image transferred to the surface of the intermediate transfer member to a surface of a recording medium.

The image forming apparatus according to this exemplary embodiment may be any one of a dry developing type image forming apparatus, a wet developing type (developing type using a liquid developer) image forming apparatus.

In the image forming apparatus according to this exemplary embodiment, for example, a part including the electrophotographic photoreceptor may have a cartridge structure (process cartridge) which is detachable from the image forming apparatus. As the process cartridge, for example, a process cartridge including the electrophotographic photoreceptor according to this exemplary embodiment is preferably applied. The process cartridge may include at least one selected from a group of, for example, the charging unit, the electrostatic latent image forming unit, the developing unit, and the transfer unit, in addition to the electrophotographic photoreceptor.

An example of the image forming apparatus according to this exemplary embodiment will be described below. However, the image forming apparatus is not limited to this example. Main components illustrated in the drawings will be described and descriptions of other components will be omitted.

Figure 4:
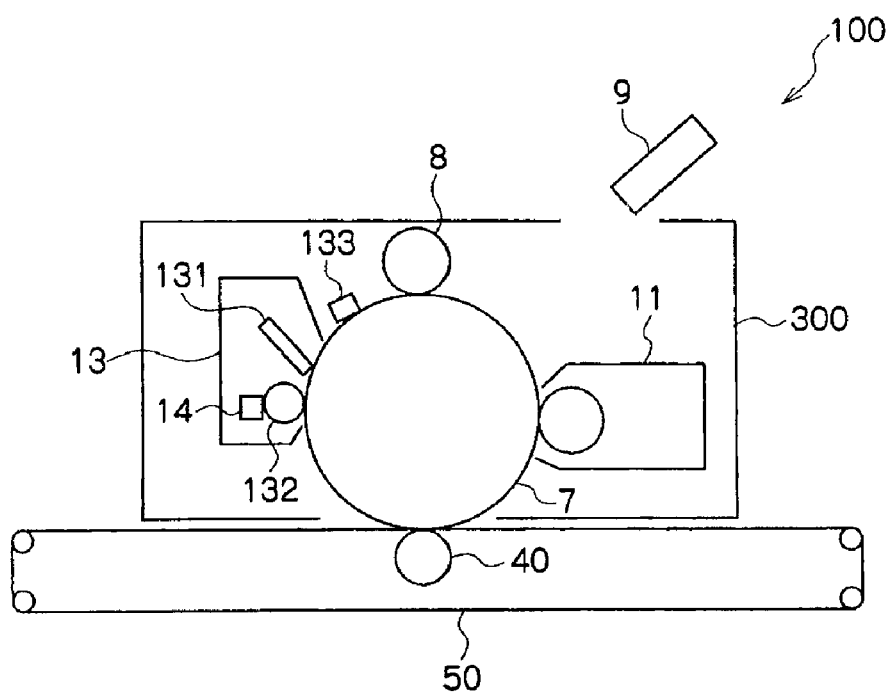
FIG. 4 is a schematic sectional view illustrating an image forming apparatus which includes a process cartridge according to the exemplary embodiment.

FIG. 4 is a schematic configuration diagram illustrating an example of the image forming apparatus according to the exemplary embodiment.

As illustrated in FIG. 4, the image forming apparatus 100 according to this exemplary embodiment includes a process cartridge 300 which includes an electrophotographic photoreceptor 7, an exposure device (example of the electrostatic latent image forming unit) 9, a transfer device (example of a primary transfer device) 40, and an intermediate transfer member 50. In the image forming apparatus 100, the exposure device 9 is disposed at a position at which the exposure device 9 may radiate light onto the electrophotographic photoreceptor 7 through an opening in the process cartridge 300. The transfer device 40 is disposed at a position opposite to the electrophotographic photoreceptor 7 with the intermediate transfer member 50 interposed between the transfer device 40 and the electrophotographic photoreceptor 7. The intermediate transfer member 50 is disposed so as to partially contact with the electrophotographic photoreceptor 7. Although not illustrated in FIG. 4, the apparatus also includes a secondary transfer device that transfers a toner image which has been transferred onto the intermediate transfer member 50 to a recording medium (for example, paper). The intermediate transfer member 50, the transfer device (primary transfer device) 40, and the secondary transfer device (not illustrated) correspond to an example of the transfer unit.

The process cartridge 300 in FIG. 4 supports, in a housing, the electrophotographic photoreceptor 7, a charging device (example of the charging unit) 8, a developing device (example of the developing unit) 11, and a cleaning device (example of a cleaning unit) 13 as a unit. The cleaning device 13 includes a cleaning blade (example of a cleaning member) 131. The cleaning blade 131 is disposed so as to contact with the surface of the electrophotographic photoreceptor 7. The cleaning member may be conductive or insulating fibrous member instead of a form of the cleaning blade 131. The cleaning member may independently use the fibrous member or may use the fibrous member along with the cleaning blade 131.

FIG. 4 illustrates an example in which a (roll-shaped) fibrous member 132 for supplying a lubricant 14 onto the surface of the electrophotographic photoreceptor 7, and a (flat brush-shaped) fibrous member 133 for assisting cleaning are included, as the image forming apparatus. However, these components may be disposed as necessary.

The components of the image forming apparatus according to this exemplary embodiment will be described below.

Charging Device

As the charging device 8, for example, a contact type charger is used. The contact type charger uses a conductive or semiconductive charging roll, a charging brush, a charging film, a charging rubber blade, a charging tube, and the like. In addition, known chargers themselves such as a non-contact type roller charger, and a scorotron charging device and a corotron charging device each utilizing corona discharge are also used.

Exposure Device

Examples of the exposure device 9 includes an optical instrument for exposure of the surface of the electrophotographic photoreceptor 7, to rays such as a semiconductor laser ray, an LED ray, and a liquid crystal shutter ray in a predetermined image-wise manner. The wavelength of the light source may be a wavelength in a range of the spectral sensitivity wavelengths of the electrophotographic photoreceptor. As the wavelengths of semiconductor lasers, near infrared wavelengths that are laser-emission wavelengths near 780 nm are predominant. However, the wavelength of the laser ray to be used is not limited to such a wavelength, and a laser having an emission wavelength of 600 nm range, or a laser having any emission wavelength in the range of 400 nm to 450 nm may be used as a blue laser. In order to form a color image, it is effective to use a planar light emission type laser light source capable of attaining a multi-beam output.

Developing Device

As the developing device 11, for example, a common developing device, in which a developer contacts or does not contact for forming an image, may be used. Such a developing device 11 is not particularly limited as long as it has the above-described functions, and may be appropriately selected according to the intended use. Examples thereof include a known developing device in which a single-component or two-component developer is applied to the electrophotographic photoreceptor 7 using a brush or a roller. Among these devices, the developing device using a development roller retaining developer on the surface thereof is preferable.

The developer used in the developing device 11 may be a single-component developer which contains only a toner, or may be a two-component developer which contains a toner and a carrier. The developer may be magnetic or may be non-magnetic. A well-known developer is applied as the developer.

Cleaning Device

As the cleaning device 13, a cleaning blade type device including the cleaning blade 131 is used.

In addition to the cleaning blade type, devices of a fur brush cleaning type and a developing and simultaneous cleaning type may be employed.

Transfer Device

Examples of the transfer device 40 include known transfer charging devices themselves, such as a contact type transfer charging device using a belt, a roller, a film, a rubber blade, or the like, and a scorotron transfer charging device and a corotron transfer charging device each utilizing corona discharge.

Intermediate Transfer Member

As the intermediate transfer member 50, a form of a belt which is imparted with the semiconductivity (intermediate transfer belt) of polyimide, polyamideimide, polycarbonate, polyarylate, polyester, rubber, or the like is used. In addition, the intermediate transfer member may also take the form of a drum, in addition to the form of a belt.

Figure 5:
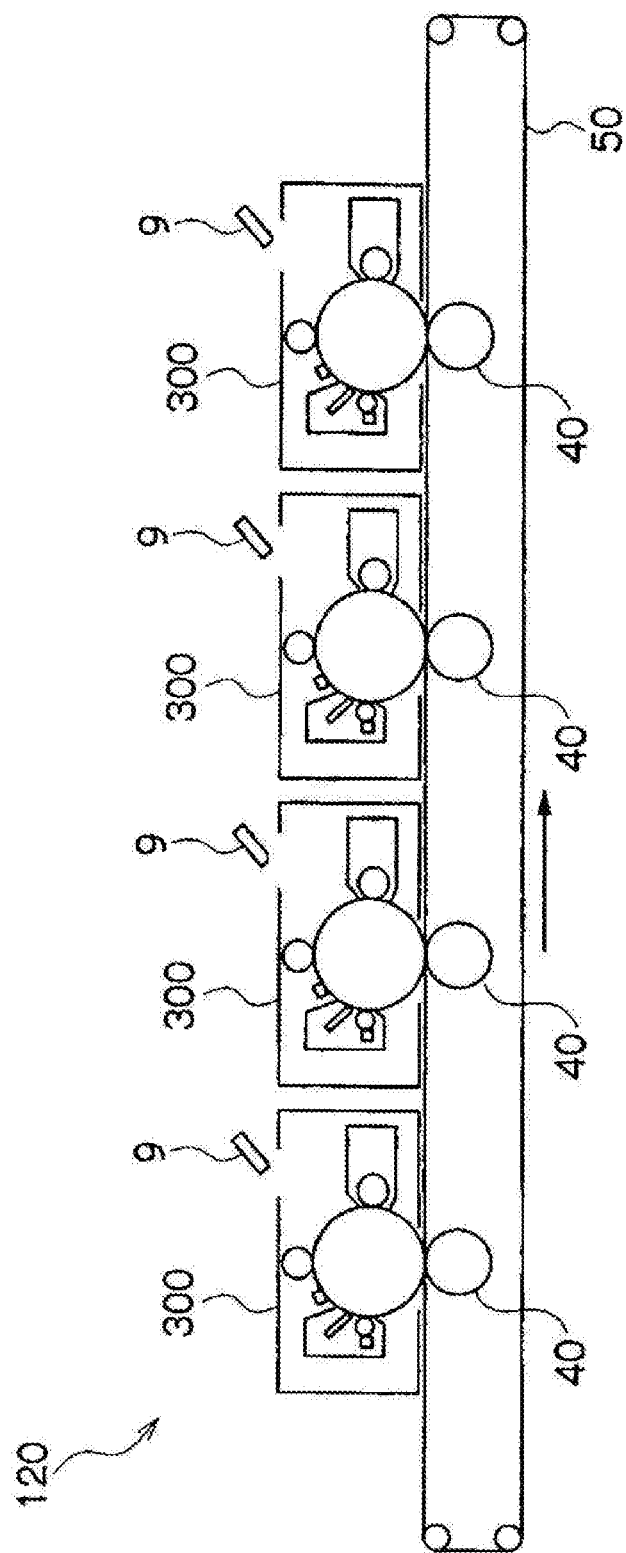
FIG. 5 is a schematic sectional view illustrating a tandem type image forming apparatus according to the exemplary embodiment.

FIG. 5 is a schematic configuration diagram illustrating another example of the image forming apparatus according to this exemplary embodiment.

An image forming apparatus 120 illustrated in FIG. 5 is a tandem multicolor image forming apparatus in which four process cartridges 300 are installed. In the image forming apparatus 120, the four process cartridges 300 on the intermediate transfer member 50 are disposed in parallel, and each process cartridge 300 has a configuration in which one electrophotographic photoreceptor to which one color is assigned is used. The image forming apparatus 120 may have a similar configuration to the image forming apparatus 100, in addition to the tandem type.

Organic EL device

Next, an organic EL device which is an example of the photoelectric conversion device will be described.

The organic EL device according to the exemplary embodiment includes a film which contains the compound (compound according to the exemplary embodiment) represented by the formula (C1).

In a case where the photoelectric conversion device is used as an organic EL device or a solar cell, the film may be any form of a single layer and a laminate layer, or may be used in any layer.

An organic electroluminescence device as an example of the organic EL device will be described in detail with reference to the drawings.

Figure 6:
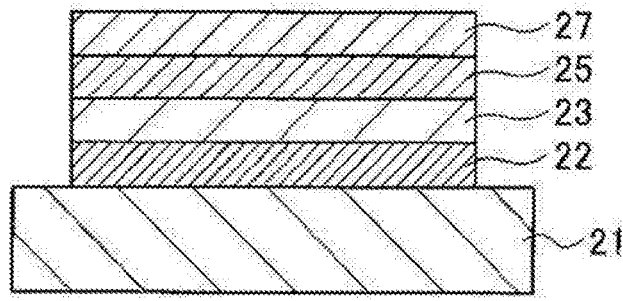
FIG. 6 is a schematic partial sectional view illustrating an example of a layer structure of an organic electroluminescence device according to the exemplary embodiment.
Figure 7:
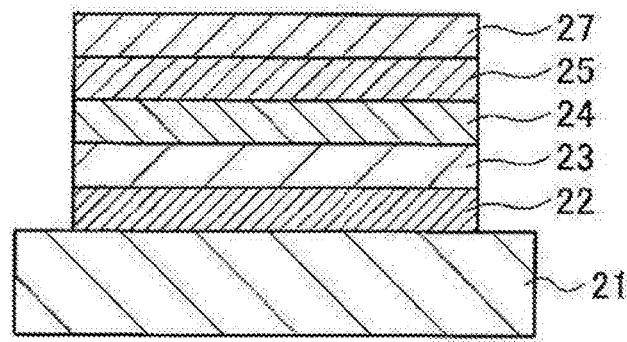
FIG. 7 is a schematic partial sectional view illustrating another example of a layer structure of an organic electroluminescence device according to the exemplary embodiment.
Figure 8:
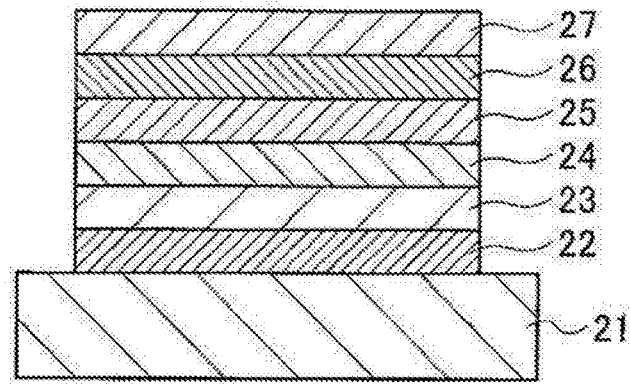
FIG. 8 is a schematic partial sectional view illustrating still another example of a layer structure of an organic electroluminescence device according to the exemplary embodiment.

FIGS. 6 to 8 are schematic sectional views illustrating an example of an organic electroluminescence device according to the exemplary embodiment. The reference sign of 21 indicates a board. The reference sign of 22 indicates an anode. The reference sign of 23 indicates a hole injection layer. The reference sign of 24 indicates a hole transporting layer. The reference sign of 25 indicates a light-emitting layer. The reference sign of 26 indicates an electron transporting layer. The reference sign of 27 indicates a cathode. The element configuration is not limited thereto.

The board 21 functions as a support member of the organic electroluminescence device. A plate of quartz or glass, a metal plate, a metal foil, a plastic film, a plastic sheet, and the like are used for the board 21. Particularly, a glass plate, or a plate of a transparent synthetic resin such as polyester, polymethacrylate, polycarbonate, and polysulfone is preferable.

In a case where a synthetic resin board is used, it is necessary that attention is paid to gas barrier properties. Thus, a method of providing a dense silicon dioxide film and the like on either side or both sides of the synthetic resin board is one of preferable methods.

The anode 22 is provided on the board 21. The anode 22 functions to inject holes to the hole injection layer 23. The anode 22 is generally constituted by metal (such as aluminum, gold, silver, nickel, palladium, and platinum) and metal oxide (such as oxide of indium and tin), metal halide (such as copper iodide), carbon black, and the like. The anode 22 is generally formed by a sputtering method, a vacuum deposition method, and the like. Metal particles of silver and the like, particles of copper iodide and the like, carbon black, conductive metal oxide particles, and the like are dispersed in an appropriate binder resin solution, and the board 21 is coated with a solution obtained by the dispersing. Thus, the anode 22 may be formed. The anode 22 may be formed by laminating layers of different materials.

The thickness of the anode 22 varies depending on the required transparency. However, generally, the thickness becomes preferable more as the transparency is high. Thus, it is preferable that transmittance of the visible light is set to be generally equal to or more than 60%, and to preferably be equal to or more than 80%. In this case, the thickness thereof is preferably from 10 nm to 1,000 nm, and more preferably from 20 nm to 500 nm.

For the purpose of laser oscillation from an end surface, and the purpose of reflecting laser between both electrodes, in a case where the anode 22 may be opaque (for example, in a case where a metal evaporated film and the like are provided), the material used for the board 21 may be used for the anode 22. Different conductive materials may be laminated on the anode 22.

In the element structure in FIGS. 6 to 8 which is exemplified as a representative example of the exemplary embodiment, the hole injection layer 23 is provided on the anode 22.

As a condition required for a material used in the hole injection layer 23, a material in which hole injection efficiency from the anode 22 is high, and an injected hole is efficiently transported is exemplified. Thus, a material in which ionization potential is low, transparency of visible light to light is high, hole mobility is high, stability is excellent, and generation of impurities functioning as a trap during preparing or using is difficult is preferable.

The hole injection layer 23 contains, for example, a hole transporting material and a binder resin. A coating-improving agent, chain polymerization monomers, oligomers may be added to the hole injection layer 23. It is also preferable to use a charge transporting material which has an alkoxysilyl group on a termination. For various purposes, silane coupling agent, aluminum coupling agent, titanate coupling agent, and the like may be additionally added. The compound according to the exemplary embodiment, that is, the compound having a structure which is represented by the above-described formula (C1) may be used as the hole transporting material.

A coating solution in which the above materials are dissolved is prepared. The anode 22 is coated with the prepared coating solution by using a method such as a spin coating method and a dip coating method. The resultant is dried to thereby form a hole injection layer 23.

The film thickness of the hole injection layer 23 is generally preferably from 5 nm to 3,000 nm, and more preferably from 10 nm to 2,000 nm.

The light-emitting layer 25 is provided on the hole injection layer 23. The light-emitting layer 25 is formed from a material in which electrons injected from the cathode 27 and holes transported from the hole injection layer 23 are rebonded to each other with high efficiency between electrodes to which an electric field is applied, and the rebonding causes emission of light with high efficiency. Examples of a material which satisfies the conditions include metal complex such as aluminum complex of 8-hydroxy quinoline; metal complex of 10-hydroxybenzo [h] quinoline; bisstyrylbenzene derivatives; bisstyrylarylene derivatives; metal complex of (2-hydroxyphenyl) benzothiazole; and silole derivatives.

The light-emitting layer material is laminated and formed on the hole injection layer 23 by using a vacuum deposition method or a coating method, for example. In a case where the coating method is used, a solvent which does not dissolve the hole injection layer 23 in practice is preferably used.

For the purpose of improving luminance efficiency of the element and of changing a luminescent color, for example, doping of laser fluorochrome such as coumarin by using aluminum complex of 8-hydroxy quinolone as a host material (J. Appl. Phys., Volume 65, pp 3610, 1989) may be performed. For example, naphthacene derivatives represented by rubrene, quinacridone derivatives, and a condensed polycyclic aromatic ring such as perylene are dopped by using metal complex such as aluminum complex of 8-hydroxy quinolone, as the host material. The doping of the above materials is performed so as to be from 0.1% by weight to 10% by weight with respect to the host material. As a method of doping the fluorochrome such as a naphthacene derivative, a quinacridone derivative, and perylene in the host material of the light-emitting layer, a method by co-deposition and a method of mixing an evaporation source at a predetermined concentration are provided.

Examples of a polymeric light-emitting layer material include a polymeric material such as poly(p-phenylenevinylene), poly[2-methoxy-5-(2-ethylhexyl oxy)-1,4-phenylene vinylene], and poly(3-alkyl thiophene) which have been exemplified above, and materials obtained by mixing polymer such as polyvinyl carbazole, with a light-emitting material and an electron transporting material.

In a case where, as with the hole injection layer, a coating method in which the hole injection layer 23 is coated by using a method such as a spin coating method and a dip coating method, so as to form a thin film is used for the materials, it is preferable that a solvent which does not dissolve the hole injection layer 23 in practice is used.

The film thickness of the light-emitting layer 25 is preferably from 10 nm to 200 nm, and more preferably from 30 nm to 100 nm.

A function separation type element in which the hole transporting layer 24 is provided between the hole injection layer 23 and the light-emitting layer 25 as illustrated in FIG. 7, or in which the electron transporting layer 26 is provided between the light-emitting layer 25 and the cathode 27 as illustrated in FIG. 8 may be provided. In the function separation type element of FIGS. 7 and 8, a material in which hole injection efficiency from the hole injection layer 23 is high, and an injected hole may be efficiently transported is preferably used as the material of the hole transporting layer 24. As the hole transporting material, the compound according to the exemplary embodiment, that is, the compound having the structure which is represented by the above-described formula (C1) may be used.

Examples of other hole transporting materials include an aromatic diamine compound to which a tertiary aromatic amine unit such as 1,1-bis(4-di-p-tolyl-aminophenyl)cyclohexane is linked; aromatic amine in which two condensed aromatic rings or more, which include two or more tertiary amines represented by 4,4'-bis[N-(1-naphthyl)-N-phenylamino]biphenyl are substituted with nitrogen atoms; aromatic triamine in which a Starburst structure is provided in derivatives of triphenylbenzene; aromatic diamine such as N,N'-diphenyl-N,N'-bis(3-methylphenyl)biphenyl-4,4'-diamine; triphenylamine derivatives which are asymmetrical in three dimensions in the entirety of a molecule; a compound in which plural aromatic diamine groups is substituted with pyrenyl groups; aromatic diamine to which a tertiary aromatic amine unit is linked in an ethylene group; aromatic diamine having a styryl structure; a substance to which a tertiary aromatic amine unit is linked in a thiophene group; Starbust type aromatic triamine; a benzyl phenyl compound; a substance to which a tertiary amine is linked in a fluorene group; a triamine compound; bisdipyridyl amino-biphenyl; N,N,N-triphenylamine derivatives; aromatic diamine having a phenoxazine structure; diaminophenyl phenanthridine derivatives; a silazane compound; silanamine derivatives; and phosphamine derivatives. The compound may be singly used or be in combination of two or more types thereof.

In addition to the above compounds, examples of the material of the hole transporting layer 24 include a polymeric material such as polyvinyl carbazole or polysilane, polyphosphazene, polyamide, polyvinyl triphenylamine, polymer having a triphenylamine skeleton, and a polymeric material such as polymethacrylate which contains aromatic amine.

The hole transporting layer 24 is formed, for example, by laminating the hole transporting material on the hole injection layer 23 by using a coating method or a vacuum deposition method. In a case of the coating method, for example, a binder resin which does not function as a trap of holes or an additive such as a coating-improving agent is added to one type of the hole transporting material or two or more types of the hole transporting materials. A resultant of addition is dissolved, and thus a coating solution is prepared. The hole injection layer 23 is coated with the prepared coating solution by using a method such as a spin coating method. A resultant of the coating is dried and thus the hole transporting layer 24 is formed. In a case of the coating method, it is preferable that a solvent which does not dissolve the hole injection layer 23 in practice is used.

Here, examples of the binder resin include polycarbonate, polyarylate, and polyester. An added amount of the binder resin is preferably equal to or more than 50% by weight.

In a case of the vacuum deposition method, the hole transporting material is put into a crucible which is installed in a vacuum container. The vacuum container is evacuated up to about $10^{-4}$ Pa by using an appropriate vacuum pump. Then, the crucible is heated so as to evaporate the hole transporting material. Thus, a hole transporting layer 24 is formed on the board 21 on which the anode 22 and the hole injection layer 23 which have been disposed so as to face the crucible have been formed.

The film thickness of the hole transporting layer 24 is preferably from 10 nm to 300 nm, and more preferably from 30 nm to 100 nm.

Generally, the above vacuum deposition method is used more.

As the compound used in the electron transporting layer 26, a compound which has large electron transporting capacity is preferable in a point of easy electron injection from the cathode 27. As the electron transporting material, the compound according to the exemplary embodiment, that is, the compound having a structure which is represented by the above-described formula (C1) may be used.

Examples of other electron transporting materials include aluminum complex of 8-hydroxy quinoline which has been already exemplified in the descriptions for the light-emitting layer material, oxadiazole derivatives (Appl. Phys. Lett., Volume 55, pp. 1489, 1989), or a material in which the above materials are dispersed in a resin such as polymethylmethacrylate (PMMA), phenanthroline derivatives, 2-t-butyl-9,10-N,N'-dicyanoanthraquinonediimine, n-type hydrogenated amorphous silicon carbide, n-type zinc sulfide, and n-type zinc selenide.

The film thickness of the electron transporting layer 26 is preferably from 5 nm to 200 nm, and more preferably from 10 nm to 100 nm.

The cathode 27 functions to inject electrons to the light-emitting layer 25. A material used in the anode 22 is used as a material used as the cathode 27. However, in order to perform electron injection with high efficiency, metal in which a work function is low is preferable, and appropriate metal such as tin, magnesium, indium, calcium, aluminum, and silver, or alloys thereof are used. As a specific example, a low work-function alloy electrode of magnesium-silver alloys, magnesium-indium alloys, aluminum-lithium alloys, and the like is exemplified.

As the film thickness of the cathode 27, generally, a range described in the descriptions for the anode 22 is exemplified.

For the purpose of protecting the cathode 27 formed of low work-function metal, it is effective that a metal layer which is stable against the atmosphere in which a work function is high is further laminated on the cathode 27. For the purpose, metal such as aluminum, silver, copper, nickel, chrome, gold, and platinum is used. A method in which a thin electrode insulating film (from 0.1 nm to 5 nm) such as LiF, $MgF_2$, and $Li_2O$ is inserted into an interface between the cathode 27 and the light-emitting layer 25 or between the cathode 27 and the electron transporting layer 26 is also effective (Appl. Phys. Lett., Volume 70, pp. 152, 1997; and IEEE Trans. Electron. Devices, Volume 44, pp. 1245, 1997).

FIGS. 6 to 8 illustrate examples of the element structure employed in the exemplary embodiment. The exemplary embodiment is not limited to the forms illustrated in FIGS. 6 to 8. For example, a structure reverse to the structure in FIG. 6 may be made. That is, the cathode 27, the light-emitting layer 25, the hole injection layer 23, and the anode 22 may be stacked on the board 21 in this order, and the organic electroluminescence device according to the exemplary embodiment may be provided between two boards of which at least one has high transparency as described above. In structures illustrated in FIGS. 7 and 8, the above constituent layers may be stacked so as to have a reversed structure. In addition, it is effective that sealing is performed by a resin, metal, and the like, a sealing layer for protecting the element from the atmosphere or water is formed, or the element has a structure in which the element itself is operated in a vacuum.

EXAMPLES

The present invention will be more specifically described based on examples and comparative examples. However, the present invention is not limited to the following examples.

A "part" described as follows is a weight basis as long as there is no particular statement.

Synthesis Example 1: Compound 4

5.0 g of 1-Naphthol and 0.35 g of Al(O-i-Pr)$_3$ are Put into a three-necked flask in which substitution with nitrogenis performed. The temperature of the flask is increased up to 120° C. under nitrogen steam, and stirring is performed for 2 hours. Then, 3.6 g of styrene is dropped into the flask for 15 minutes, and then stirring is performed for 3 hours. After cooling, 100 ml of toluene, and 100 ml of distilled water are added, and washing and liquid separation is performed. An organic layer is dried with anhydrous sodium sulfate, and the solvent is removed under a decompressed state.

20 ml of methanol, 0.1 g of CuCl, and 0.23 g of tetramethylenediamine are added, and stirring is performed for 16 hours in a state where oxygen in the liquid is subjected to bubbling. 100 ml of toluene, and 100 ml of distilled water are added, and washing and liquid separation is performed. An organic layer is dried with anhydrous sodium sulfate. 10 g of silica gel is added, and stirring is performed for 10 minutes. Then, the silica gel is filtered, and the solvent is removed under a decompressed state. Then, recrystallization is performed by using 10 ml of toluene and 15 ml of methanol, thereby obtaining 5 g of Compound 4.

Figure 9:
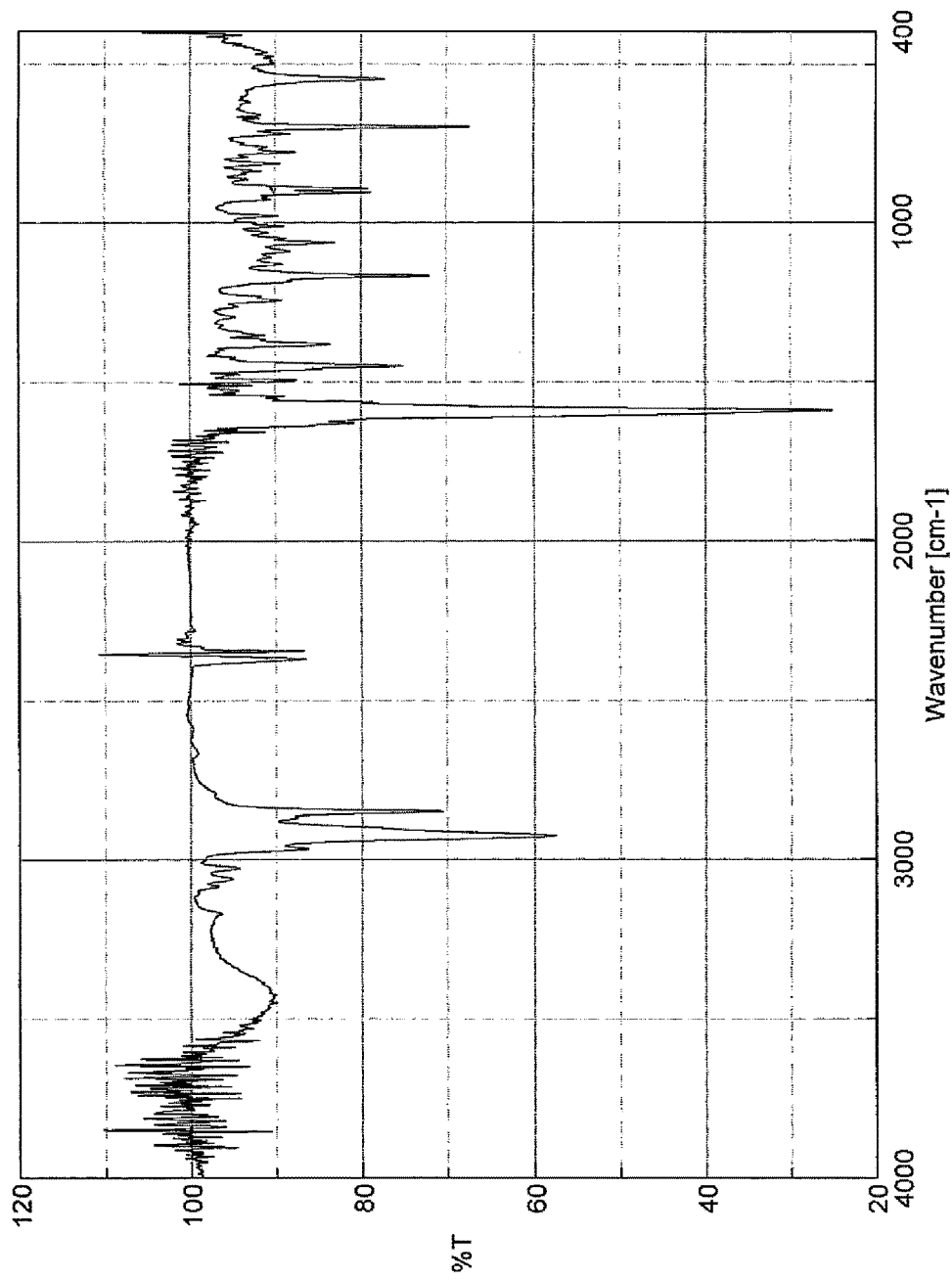
FIG. 9 is a graph illustrating IR spectrum of Compound 4 synthesized in Example.

FIG. 9 illustrates IR spectrum of obtained Compound 4.

Synthesis Example 2: Compound 17

3.0 g of ortho-t-butylphenol and 0.2 g of Al(O-i-Pr)$_3$ are put into a three-necked flask in which substitution with nitrogen is performed. The temperature of the flask is increased up to 120° C. under nitrogen steam, and stirring is performed for 1 hour. Then, 2.1 g of styrene is dropped into the flask for 10 minutes, and then stirring is performed for 6 hours. After cooling, 50 ml of toluene, and 50 ml of distilled water are added, and washing and liquid separation is performed. An organic layer is dried with anhydrous sodium sulfate, and the solvent is removed under a decompressed state.

10 ml of methanol, 0.06 g of CuCl, and 0.14 g of tetramethylenediamine are added, and stirring is performed for 16 hours in a state where oxygen in the liquid is subjected to bubbling. 50 ml of toluene, and 50 ml of distilled water are added, and washing and liquid separation is performed. An organic layer is dried with anhydrous sodium sulfate. 5 g of silica gel is added, and stirring is performed for 10 minutes. Then, the silica gel is filtered, and the solvent is removed under a decompressed state. Then, recrystallization is performed by using 5 ml of toluene and 10 ml of methanol, thereby obtaining 0.8 g of Compound 17.

FIG. 10 illustrates IR spectrum of obtained Compound 17.

Example 1

Preparation of Photoreceptor 1

A mixture of the following materials is obtained: 1.2 parts (HOGaPC:ClGaPC=5:5 (weight ratio)) of a hydroxy gallium phthalocyanine pigment (HOGaPC) and a chlorogallium phthalocyanine pigment (ClGaPC) as the charge generating material; 46.8 parts of a bisphenol Z polycarbonate resin (PCZ, viscosity average molecular weight:50,000) as a binder resin; 15 parts of Compound 4 (electron transporting material) obtained in Synthesis Example 1; 37 parts of a hole transporting material represented by the exemplary compound (HT-7); and 250 parts of tetrahydrofuran as a solvent. The hydroxy gallium phthalocyanine pigment has diffraction peak at a position at which the Bragg angle (2θ±0.20) in the X-ray diffraction spectrum using a Cuκα characteristic X-ray is at least 7.3°, 16.0°, 24.9°, or 28.0°. The chlorogallium phthalocyanine pigment has diffraction peak at a position at which the Bragg angle (2θ±0.20) in the X-ray diffraction spectrum using a Cuκα characteristic X-ray is at least 7.4°, 16.6°, 25.5°, or 28.3°. The mixture is dispersed in a sand mill by using glass beads of 1 mmϕ, for 4 hours. Thus, a coating liquid for forming a photoreceptive layer is obtained.

An aluminum substrate which is 30 mm in diameter and 244.5 mm in length is coated with the coating liquid for forming a photosensitive layer by using a dip coating method. Drying is performed at 140° C. for 30 minutes, and thus, a single-layer type photosensitive layer having a thickness of 30 μm is obtained.

With the above processes, an electrophotographic photoreceptor (photoreceptor A1) in Example 1 is prepared.

Compatibility Recognition Sample

In the preparation process of the coating liquid for forming a photosensitive layer, a compatibility recognition sample is prepared by performing similar operations except that the charge generating material (hydroxy gallium phthalocyanine pigment and chlorogallium phthalocyanine pigment) is not added.

Examples 2 to 12

Similarly to Example 1, a photoreceptor is prepared except that the electron transporting material, the hole transporting material, the charge generating material, and the binder resin which are used in Example 1 are changed to the material type shown in the following Table 1. Similarly to Example 1, a compatibility recognition sample is prepared except that the electron transporting material, the hole transporting material, and the binder resin which are used in Example 1 are changed to the material type shown in the following Table 1.

Comparative Example 1

A comparative photoreceptor B1 is prepared similarly to Example 1, except that the electron transporting material used in Example 1 is changed to a compound represented by the exemplary compound (ET-5).

Similarly to Example 1, a compatibility recognition sample is prepared except that the electron transporting material used in Example 1 is changed to a compound represented by the exemplary compound (ET-5).

Comparative Example 2

A comparative photoreceptor B2 is prepared similarly to Example 1, except that the electron transporting material used in Example 1 is changed to a compound represented by the exemplary compound (ET-6).

Similarly to Example 1, a compatibility recognition sample is prepared except that the electron transporting material used in Example 1 is changed to a compound represented by the exemplary compound (ET-6).

TABLE 1

| | | Electron Transporting Material | | Hole Transporting Material | | Charge Generating Material | | | | Binder Resin | |
|---|---|---|---|---|---|---|---|---|---|---|---|
| | Photoreceptor | Type | Amount | Type | Amount | Type | Amount | Type | Amount | Type | Amount |
| Example 1 | Photoreceptor A1 | 4 | 15 | HT-7 | 37 | HOGaPC | 0.6 | ClGaPC | 0.6 | PCZ | 46.8 |
| Example 2 | Photoreceptor A2 | 17 | 15 | HT-7 | 37 | HOGaPC | 0.6 | ClGaPC | 0.6 | PCZ | 46.8 |
| Example 3 | Photoreceptor A3 | 5 | 15 | HT-7 | 37 | HOGaPC | 0.6 | ClGaPC | 0.6 | PCZ | 46.8 |
| Example 4 | Photoreceptor A4 | 10 | 15 | HT-7 | 37 | HOGaPC | 0.6 | ClGaPC | 0.6 | PCZ | 46.8 |
| Example 5 | Photoreceptor A5 | 101/22/17 | 8/3/4 | HT-7 | 37 | HOGaPC | 0.6 | ClGaPC | 0.6 | PCZ | 46.8 |
| Example 6 | Photoreceptor A6 | 17/ET-1/202 | 9/3/3 | HT-7 | 37 | HOGaPC | 0.6 | ClGaPC | 0.6 | PCZ | 46.8 |

TABLE 1-continued

|  | Photoreceptor | Electron Transporting Material | | Hole Transporting Material | | Charge Generating Material | | | | Binder Resin | |
|---|---|---|---|---|---|---|---|---|---|---|---|
|  |  | Type | Amount | Type | Amount | Type | Amount | Type | Amount | Type | Amount |
| Example 7 | Photoreceptor A7 | 4 | 15 | HT-7 | 37 | HOGaPC | 1 | — | — | PCZ | 47 |
| Example 8 | Photoreceptor A8 | 4 | 10 | HT-7 | 42 | HOGaPC | 0.6 | ClGaPC | 0.6 | PCZ | 46.8 |
| Example 9 | Photoreceptor A9 | 4 | 15 | HT-1 | 37 | HOGaPC | 0.6 | ClGaPC | 0.6 | PCZ | 46.8 |
| Example 10 | Photoreceptor A10 | 4 | 15 | HT-2 | 37 | HOGaPC | 0.6 | ClGaPC | 0.6 | PCZ | 46.8 |
| Example 11 | Photoreceptor A11 | 4 | 15 | HT-3 | 37 | HOGaPC | 0.6 | ClGaPC | 0.6 | PCZ | 46.8 |
| Example 12 | Photoreceptor A12 | 4 | 15 | HT-8 | 37 | HOGaPC | 0.6 | ClGaPC | 0.6 | PCZ | 46.8 |
| Comparative Example 1 | Photoreceptor B1 | ET-5 | 15 | HT-7 | 37 | HOGaPC | 0.6 | ClGaPC | 0.6 | PCZ | 46.8 |
| Comparative Example 2 | Photoreceptor B2 | ET-6 | 15 | HT-7 | 37 | HOGaPC | 0.6 | ClGaPC | 0.6 | PCZ | 46.8 |

Evaluation

The following evaluations are performed for the electrophotographic photoreceptors obtained in the above-described manner.

Residual potential and charging characteristics

Residual potential and charging characteristics are evaluated by using the following method.

The obtained photoreceptor is mounted in an image forming apparatus (product manufactured by Brother Corporation, HL-2240D), and modification to an apparatus for measuring a potential is performed. Specifically, instead of the developing device, a surface potential measuring probe (Trek Corporation, Model 555P-1) is installed so as to face the photoreceptor. The installed surface potential measuring probe is connected to a surface potential meter (Trek Corporation, TREK 334), and thus potential measurement is performed.

Then, a photoreceptor surface potential (surface potential of the photoreceptor in which a latent image of solid density is formed by the exposure device) when an image of solid density is output is measured under an environment of a room temperature of 30° C. and a humidity of 90%. The measured potential is set as a potential-after-exposing VL-b. A photoreceptor surface potential in a state of non-exposing (surface potential of the photoreceptor when the exposure device is set to be OFF) is measured, and the measured potential is set as a potential-after-exposing VH-b.

Then, 10,000 pieces of A4 image which has image density of 5% are formed under an environment of a room temperature of 30° C. and a humidity of 90%, and measurement similar to the above descriptions is performed. Thus, the measured potentials are set as a potential-after-exposing VL-a and a potential-after-exposing VH-a, respectively.

Determination, that is, evaluation of the residual potential is performed by using a changed amount between before image formation and after the image formation, that is, a value of |VL-a|-|VL-b|. The evaluation is determined based on the following criteria.

Evaluation Criteria
A: less than 5 V
B: equal to or more than 5 V and less than 10 V
C: equal to or more than 10 V and less than 15 V
D: equal to or more than 15 V Determination, that is, evaluation of the charging characteristics is performed by using a changed amount between before image formation and after the image formation, that is, a value of |VH-a|-|VH-b|. The evaluation is determined based on the following criteria.

Evaluation Criteria
A: less than 10 V
B: equal to or more than 10 V and less than 15 V
C: equal to or more than 15 V and less than 20 V
D: equal to or more than 20 V Image Quality Image quality is evaluated by using the following method.

After the residual potential and the charging characteristics are evaluated, an A4 image having image density of 0% is printed under an environment of room temperature of 32° C. and humidity of 90%. Evaluation is performed by using the number of black spots which are obtained by printing on a sheet. Evaluation criteria are as follows.

Evaluation Criteria
A: occurrence of a black spot is not recognized
B: a few black spot may be recognized by using a magnifier of 10 times (there is no problem in actual use)
C: a black spot may be recognized by using a magnifier of 10 times (there is a probability of a problem occurring in a color device having tight SPEC)
D: a black spot may be visually recognized (there is a problem in actual use)

Compatibility (Photosensitive Layer Uniformity)

The compatibility is evaluated by the following method.

A compatibility recognition sample is prepared, and a sample obtained by causing the compatibility recognition sample to pass through a filter of 0.45 μm is prepared. The prepared compatibility recognition sample and the prepared sample are evaluated. Evaluation criteria are as follows.

Evaluation Criteria
A: both of the samples have no problem because both of the samples are transparent regardless of whether or not filtering is performed.
B: level at which results are different depending on whether or not filtering is performed, but both of the samples have no problem.
C: turbidity in the sample in which filtering is not performed is observed.
D: turbidity in the sample in which filtering is not performed is observed and clogging occurs when filtering is performed.

TABLE 2

| | Residual potential | Charging characteristics | Image quality | Compatibility |
|---|---|---|---|---|
| Example 1 | A | A | A | A |
| Example 2 | A | A | A | A |
| Example 3 | B | A | A | A |
| Example 4 | A | A | A | A |
| Example 5 | A | B | A | A |
| Example 6 | A | A | B | B |
| Example 7 | A | A | A | A |
| Example 8 | B | A | A | A |
| Example 9 | A | A | A | A |
| Example 10 | A | A | A | A |
| Example 11 | A | A | A | A |
| Example 12 | A | A | A | A |
| Comparative Example 1 | D | D | D | D |
| Comparative Example 2 | C | D | C | C |

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A compound having a structure represented by the following formula (C1):

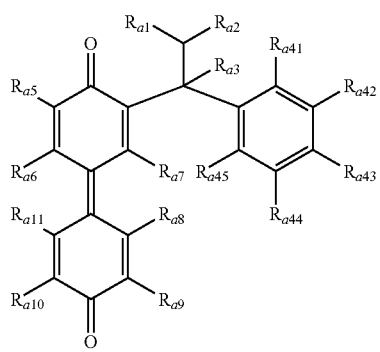

Formula (C1)

wherein $R_{a1}$, $R_{a2}$, $R_{a3}$, $R_{a41}$, $R_{a42}$, $R_{a43}$, $R_{a44}$, $R_{a45}$, $R_{a5}$, $R_{a6}$, $R_{a7}$, $R_{a8}$, $R_{a9}$, $R_{a10}$, and $R_{a11}$ each independently represent a hydrogen atom, an alkyl group, an alkenyl group, an alkynyl group, an alkoxy group, an aralkyl group, an aryl group, a cyano group, a halogen atom, or a group obtained by combining two or more of the above groups, and a combination of $R_{a1}$ and $R_{a2}$, $R_{a41}$ and $R_{a42}$, $R_{a42}$ and $R_{a43}$, $R_{a43}$ and $R_{a44}$, $R_{a44}$ and $R_{a45}$, $R_{a5}$ and $R_{a6}$, $R_{a8}$ and $R_{a9}$, or $R_{a10}$ and $R_{a11}$ each independently may form a ring.

2. The compound according to claim 1, wherein the compound has a structure represented by the following formula (C2):

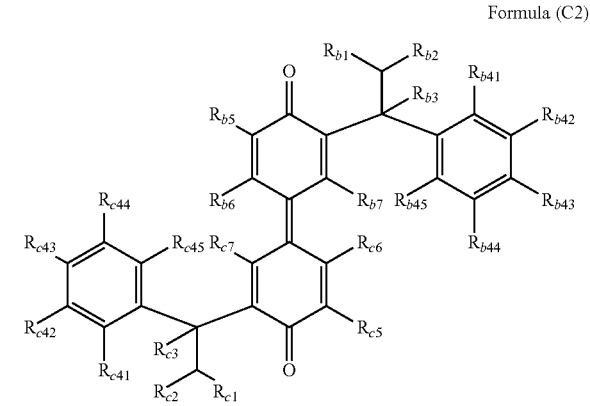

Formula (C2)

wherein $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, $R_{b7}$, $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ each independently represent a hydrogen atom, an alkyl group, an alkenyl group, an alkynyl group, an alkoxy group, an aralkyl group, an aryl group, a cyano group, a halogen atom, or a group obtained by combining two or more of the above groups, and a combination of $R_{b1}$ and $R_{b2}$, $R_{b41}$ and $R_{b42}$, $R_{b42}$ and $R_{b43}$, $R_{b43}$ and $R_{b44}$, $R_{b44}$ and $R_{b45}$, $R_{b5}$ and $R_{b6}$, $R_{c1}$ and $R_{c2}$, $R_{c41}$ and $R_{c42}$, $R_{c42}$ and $R_{c43}$, $R_{c43}$ and $R_{c44}$, $R_{c44}$ and $R_{c45}$, or $R_{c5}$ and $R_{c6}$ each independently may form a ring.

3. An electrophotographic photoreceptor comprising:
an electroconductive substrate; and
an undercoat layer and an organic photosensitive layer which are provided on the electroconductive substrate,
wherein the undercoat layer or the organic photosensitive layer contains the compound according to claim 1.

4. The electrophotographic photoreceptor according to claim 3,
wherein the organic photosensitive layer contains a binder resin, a charge generating material, a hole transporting material, and the compound.

5. The electrophotographic photoreceptor according to claim 4,
wherein a weight ratio of the hole transporting material and the compound (the hole transporting material:the compound) contained in the organic photosensitive layer is in a range of 1:1 to 9:1.

6. The electrophotographic photoreceptor according to claim 3,
wherein the compound has a structure represented by the following formula (C2):

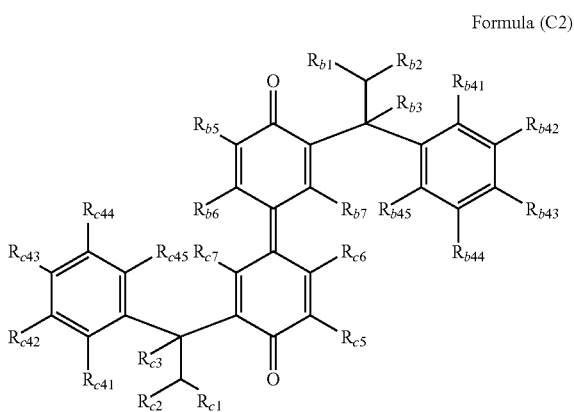

Formula (C2)

wherein $R_{b1}$, $R_{b2}$, $R_{b3}$, $R_{b41}$, $R_{b42}$, $R_{b43}$, $R_{b44}$, $R_{b45}$, $R_{b5}$, $R_{b6}$, $R_{b7}$, $R_{c1}$, $R_{c2}$, $R_{c3}$, $R_{c41}$, $R_{c42}$, $R_{c43}$, $R_{c44}$, $R_{c45}$, $R_{c5}$, $R_{c6}$, and $R_{c7}$ each independently represent a hydrogen atom, an alkyl group, an alkenyl group, an alkynyl group, an alkoxy group, an aralkyl group, an aryl group, a cyano group, a halogen atom, or a group obtained by combining two or more of the above groups, and a combination of $R_{b1}$ and $R_{b2}$, $R_{b41}$ and $R_{b42}$, $R_{b42}$ and $R_{b43}$, $R_{b43}$ and $R_{b44}$, $R_{b44}$ and $R_{b45}$, $R_{b5}$ and $R_{b6}$, $R_{c1}$ and $R_{c2}$, $R_{c41}$ and $R_{c42}$, $R_{c42}$ and $R_{c43}$, $R_{c43}$ and $R_{c44}$, $R_{c44}$ and $R_{c45}$, or $R_{c5}$ and $R_{c6}$ each independently may form a ring.

7. The electrophotographic photoreceptor according to claim 6,
wherein the organic photosensitive layer contains a binder resin, a charge generating material, a hole transporting material, and the compound.

8. A process cartridge that is detachable from an image forming apparatus, the cartridge comprising:
the electrophotographic photoreceptor according to claim 6.

9. A process cartridge that is detachable from an image forming apparatus, the cartridge comprising:
the electrophotographic photoreceptor according to claim 3.

\* \* \* \* \*